(12) United States Patent
Vander Jagt et al.

(10) Patent No.: US 8,980,954 B2
(45) Date of Patent: Mar. 17, 2015

(54) SUBSTITUTED CIS- AND TRANS-STILBENES AS THERAPEUTIC AGENTS

(75) Inventors: David L. Vander Jagt, Albuquerque, NM (US); Lorraine M. Deck, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 1920 days.

(21) Appl. No.: 11/789,583

(22) Filed: Apr. 25, 2007

(65) Prior Publication Data

US 2007/0249647 A1 Oct. 25, 2007

Related U.S. Application Data

(60) Provisional application No. 60/794,765, filed on Apr. 25, 2006.

(51) Int. Cl.
```
A61K 31/035    (2006.01)
A61P 25/28     (2006.01)
C07C 39/23     (2006.01)
A61K 31/381    (2006.01)
A61K 31/44     (2006.01)
A61K 31/525    (2006.01)
A61K 31/66     (2006.01)
C07D 213/30    (2006.01)
C07D 333/16    (2006.01)
```
(52) U.S. Cl.
CPC ............... A61K 31/381 (2013.01); A61K 31/44 (2013.01); A61K 31/525 (2013.01); A61K 31/66 (2013.01); C07D 213/30 (2013.01); C07D 333/16 (2013.01)
USPC .......................................... 514/733; 514/764

(58) Field of Classification Search
CPC ... A61K 31/44; A61K 31/381; A61K 31/035; C07D 333/10; C07D 211/68; C07C 39/23
USPC ........... 514/277, 438, 733, 720, 34, 492, 109, 514/27, 49, 262.1, 8, 406, 283, 559, 251, 514/651, 78, 764; 424/623, 94.63, 85.7; 546/339; 549/78
See application file for complete search history.

(56) References Cited

U.S. PATENT DOCUMENTS

| | | | |
|---|---|---|---|
| 5,852,028 A * | 12/1998 | Suto et al. ................ | 514/275 |
| 5,869,461 A * | 2/1999 | Cheng et al. .............. | 514/43 |
| 5,891,924 A * | 4/1999 | Aggarwal .................. | 514/679 |
| 2003/0171429 A1* | 9/2003 | Chen et al. ................ | 514/475 |

OTHER PUBLICATIONS

Kung, "Novel Stilbenes as Probes for Amyloid Plaques", JACS, 2001, 123, pp. 12740-12741.*
Yamamoto, Y.; Gaynor, R.B. Therapeutic potential of inhibition of the NF-kappaB pathway in the treatment of inflammation and cancer. J. Clin. Invest. 2001, 107, 135-142.
Kim, H.J.; Hawke, N.; Baldwin, A.S. NF-KB and IKK as therapeutic targets in cancer. Cell Death Different. 2006, advanced online publication.
Kaltschmidt, B.; Widera, D.; Kaltschmidt, C. Signaling via NF-KB in the nervous system. Biochim. Biophys. Acta 2005, 1745, 287-299.
Viatour, P.; Merville, M-P.; Bours, V.; Chariot, A. Phosphorylation of NF 10 kappaB and IkappaB proteins: implications in cancer and inflammation. Trends Biochem. Sci. 2005, 30, 43-52.
Kumar, A.; Takada, Y.; Boriek, A.M.; Aggarwal, B.B. Nuclear factor-KB: its role in health and disease. J. Mol. Med. 2004, 82, 434-448.
Hiscott, J.; Kwon, H.; Genin, P. Hostile takeovers: viral appropriation of the 15 NF-kappaB pathway. J. Clin. Invest. 2001, 107, 143-151.
Barkett, M.; Gilmore, T. Control of apoptosis by Rel/NF-kappaB transcription factors. Oncogene 1999, 18, 6910-6924.
Karin, M.; Greten, F.R. NF-KB: linking inflammation and immunity to cancer development and progression. Nature Rev. Immunol. 2005, 5, 749-759.
Hellmann, O.; Baumann, B.; de Lorenzi, R.; Muhammad, S.; Zhang, W.; Kleesiek, J.; Malfertheiner, M.; Kohrmann, M.; Potrovita, I.; Maegele, I.; Beyer, C.; Burke, J.R.; Hasan, M.T.; Bujard, H.; Wirth, T.; Pasparakis, M.; Schwaninger, M. IKK mediates ischemia-induced neuronal death. Nat. Med. 2005, 11, 1322-1329.
Schmitz, M.L.; Mattioli, I.; Buss, H.; Kracht, M. NF—x B: a multifaceted transcription factor regulated at several levels. ChemBioChem 2004, 5, 1348-1358.
http://people.bu.edu/gilmore/nf-kb/inhibitors.
Dore, S. Unique properties of polyphenol stilbenes in the brain: more than direct antioxidant actions; gene/protein regulatory activity. Neurosignals 2005, 14, 61-70.
Kundu, J.K.; Surh, Y-J. Molecular basis of chemoprevention by resveratrol: NF—KB and AP-1 as potential targets. Mut. Res. 2004, 555, 65-80.
Shimizu, M.; Weinstein, B. Modulation of signal transduction by tea catechins and related phytochemicals. Mut. Res. 2005, 591, 147-160.
Renaud, S.; de Lorgeril, M. Wine, platelets, and the French paradox for coronary heart disease. Lancet 1992, 339, 1523-1526.
Jang, M.; Cai, L.; Udeani, G.O.; Slowing, K.V.; Thomas, C.F.; Beecher, C.W.; Fong, H.H.; Farnsworth, N.R.; Kinghorn, A.D.; Mehta, R.G.; Moon, R.C.; Pezzuto, J.M. Cancer chemopreventive activity of resveratrol, a natural product derived from grapes. Science 1997, 275, 218-220.
Ovesna, Z.; Horvathova-Kozics, K. Structure-activity relationship of trans-resveratrol and its analogs. Neoplasma 2005, 52, 450-455.
Orallo, F. Comparative studies of the antioxidant effects of cis- and trans-resveratrol. Curr. Med. Chem. 2006, 13, 87-98.

(Continued)

*Primary Examiner* — Sreeni Padmanabhan
*Assistant Examiner* — Sahar Javanmard
(74) *Attorney, Agent, or Firm* — Henry D. Coleman; R. Neil Sudol

(57) ABSTRACT

The present invention relates to method(s) of treating a subject afflicted with cancer or a precancerous condition, an inflammatory disease or condition, and/or stroke or other ischemic disease or condition, the method comprising administering to the subject or patient in need a composition comprising a therapeutically effective amount of a substituted cis or trans-stilbene.

16 Claims, 13 Drawing Sheets

(56) References Cited

OTHER PUBLICATIONS

Lu, M.; Cai, Y.J.; Fang, J.G.; Zhou, Y.L.; Liu, Z.L.; Wu, L.M. Efficiency and structure-activity relationship of the antioxidant action of resveratrol and its analogs. Pharmazie 2002, 57, 474-478.

Stojanovic, S.; Sprinz, H.; Brede, O. Efficiency and mechanism of the antioxidant action of trans-resveratrol and its analogues in the radical liposome oxidation. Arch. Biochem. Biophys. 2001, 391, 79-89.

Stivala, L.A.; Savio, M.; Carafoli, F.; Perucca, P.; Bianchi, L.; Maga, G.; Forti, L.; Pagnoni, U.M.; Albini, A.; Prosperi, E.; Vannini, V. Specific structural determinants are responsible for the antioxidant activity and the cell cycle effects of resveratrol. J. Biol. Chem. 2001, 276, 22586-22594.

Chung, M.I.; Teng, C.M.; Cheng, K.L.; Ko, F.N.; Lin, C.N. An antiplatelet principle of *Veratrum formosanum*. Planta Med. 1992, 58, 274-276.

Fremont, L.; Gozzelino, M.T.; Linard, A. Response of plasma lipids to dietary cholesterol and wine polyphenols in rats fed polyunsaturated fat diets. Lipids 2000, 35, 991-999.

Murias, M.; Handler, N.; Erker, T.; Pleban, K.; Ecker, G.; Saiko, P.; Szekeres, T.; Jager, W. Resveratrol analogues as selective cyclooxygenase-2 inhibitors: synthesis and structure-activity relationship. Bioorg. Med. Chem. 2004, 12, 5571-5578.

Shay, N.F.; Banz, W.J. Regulation of gene transcription by botanicals: novel regulatory mechanisms. Annu. Rev. Nutr. 2005, 25, 297-315.

Juan, S.H.; Cheng, T.H.; Lin, H.C.; Chu, Y.L.; Lee, W.S. Mechanism of concentration-dependent induction of heme oxygenase-1 by resveratrol in human aortic smooth muscle cells. Biochem. Pharmacol. 2005, 69, 41-48.

Kundu, J.K.; Shin, Y.K.; Surh, Y.J. Resveratrol inhibits phorbol ester-induced expression of COX-2 and activation of NF-kappaB in mouse skin by blocking IkappaB activity. Carcinogenesis 2006, Epub ahead of print.

Lee, B.; Moon, S-K. Resveratrol inhibits TNF-K-induced proliferation and matrix metalloproteinase expression in human vascular smooth muscle cells. J. Nutr. 2005, 135, 2767-2773.

Liao, H.F.; Kuo, C.D.; Yang, Y.C.; Lin, C.P.; Tai, H.C.; Chen, Y.Y.; Chen, Y.J. Resveratrol enhances radiosensitivity of human non-small cell lung cancer NCI-H838 cells accompanied by inhibition of nuclear factor-kappa B activation. J. Radiat. Res. (Tokyo) 2005, 46, 387-393.

Bi, X.L.; Yang, J.Y.; Dong, Y.X.; Wang, J.M.; Cui, Y.H.; Ikeshima, T.; Zhao. Y.Q.; Wu, C.F. Resveratrol inhibits nitric oxide and TNF-alpha production by lipopolysaccharide-activated microglia. Int. Immunopharmacol. 2005, 5, 185 193.

Bellucci, G.; Chiappe, C.; Lo Moro, G. Crown ether catalyzed stereospecific synthesis of Z- and E-stilbenes by Wittig reaction in a solid-liquid two-phase system. Tetrahedron Lett. 1996, 37, 4225-4228.

Lion, C.J.; Matthews, C.S.; Stevens, M.F.G.; Westwell, A.D. Synthesis, antitumor evaluation, and apoptosis-inducing activity of hydroxylated (E)-stilbenes. J. Med. Chem. 2005, 48, 1292-1295.

Kang, G.; Kong, P.J.; Yuh, Y.J.; Lim, S.Y.; Yim, S.V.; Chun, W.; Kim, S.S. Curcumin suppresses lipopolysaccharide-induced cyclooxygenase-2 expression by inhibiting activator protein 1 and nuclear factor kappab bindings in BV2 microglial cells. J. Parmaco.1 Sci. 2004, 94, 325-328.

Wieder, T.; Prokop, A.; Bagci, B.; Essmann, F.; Bernicke, D.; Schulze-Osthoff, K.; Dorken, B.; Schmalz, H.G.; Daniel, P.T.; Henze, G. Piceatannol, a hydroxylated analog of the chemopreventive agent resveratrol, is a potent inducer of apoptosis in the lymphoma cell line BJAB and in primary, leukemic lymphoblasts. Leukemia 2001, 15, 1735-1742.

Ashikawa, K.; Majumdar, S.; Banerjee, S.; Bharti, A.C.; Shishodia, S.; Aggarwal, B.B. Piceatannol inhibits TNF-induced NF-xB activation and NF-xB-mediated gene expression through suppression of IxBx kinase and p65 phosphorylation. J. Immunol. 2002, 169, 6490-6497.

Rimando, A.M.; Cuendet, M.; Desmarchelier, C.; Mehta, R.G.; Pezzuto, J.M.; Duke, S.O. Cancer chemopreventive and antioxidant activities of pterostilbene, a naturally occurring analogue of resveratrol. J. Agric. Food Chem. 2002, 50, 3453-3457.

Tolomeo, M.; Grimaudo, S.; Di Cristina, A.; Roberti, M.; Pizzirani, D.; Meli, M.; Dusonchet, L.; Gebbia, N.; Abbadessa, V.; Crosta, L.; Barucchello, R.; Grisolia, G.; Invidiata, F.; Simoni, D. Pterostilbene and 3'-hydroxypterostilbene are effective apoptosis-inducing agents in MDR and BCR-ABL-expressing leukemia cells. Int. J. Biochem. Cell. Biol. 2005, 37, 1709-1726.

Mann, S.K.; Mukhopadhyay, A.; Aggarwal, B.B. Resveratrol suppresses TNF induced activation of nuclear transcription factors NF-kB, activator protein-1, and apoptosis: potential role of reactive oxygen intermediates and lipid peroxidation. J. Immunol. 2000, 164, 6509-6519.

Sizemore, N.; Lerner, N.; Dombrowski, N.; Sakurai, H.; Stark, G.R. Distinct roles of the IKB kinase a and b in liberating nuclear factor xB (NF-xB) from IB 25 and in phosphorylating the p65 subunit of NF-xB. J. Biol. Chem. 2002, 277, 3863-3869.

Schlesier, K.; Harwat, M.; Bohm, V.; Bitsch, R. Assessment of antioxidant activity by using different in vitro methods. Free Rad. Res. 2002, 36, 177-187.

Re, R.; Pellegrini, N.; Proteggente, A.; Pannala, A.; Yang, M.; Rice-Evans, C. Antioxidant activity applying an improved ABTS radical cation decolorization assay. Free Rad. Biol. Med. 1999, 26, 1231-1237.

Benzie, I.F.; Strain, J.J. Ferric reducing/antioxidant power assay: direct measure of total antioxidant activity of biological fluids and modified version for simultaneous measurement of total antioxidant power and ascorbic acid concentrations. Methods Enzymol. 1999, 299, 15-27.

Begum, S.D.; Parthasarathi, J. A convenient synthesis of homobutein. Ind. J. Chem., Sect. B 1988, 27B, 464.

\* cited by examiner

SUBSTITUTED CIS- AND TRANS-STILBENES AS THERAPEUTIC AGENTS

RELATED APPLICATIONS AND FUNDING

This application claims the benefit of priority of provisional application No. U.S. 60/794,765, filed Apr. 25, 2007.

The present invention was made with government support under Grant No. EY13695, awarded by the National Eye Institute, and Grant No. BC043125, awarded by the U.S. Army/DOD Breast Cancer Program. The Government may have certain rights in this invention.

FIELD OF THE INVENTION

The present invention relates to method(s) of treating a subject afflicted with cancer or a precancerous condition, an inflammatory disease or condition, and/or stroke or other ischemic disease or condition, the method comprising administering to the subject or patient in need a composition comprising a therapeutically effective amount of a substituted cis or trans-stilbene.

BACKGROUND

The nuclear factor κB (NF-κB) family of transcription factors in mammals consists of homo- and hetero-dimeric combinations of five related proteins (p50, p52, p65/RelA, c-Rel, and RelB) that have a marked influence on the expression of numerous genes involved in immunity and inflammation, as well as cellular stress responses, growth, and apoptosis. Diverse pathways activate NF-κB, and control of these pathways is increasingly viewed as an approach to chemotherapy in the many diseases that have an associated inflammatory component, including cancer, stroke, Alzheimer's disease and diabetes.[1-10] Activation of NF-κB occurs through multiple pathways. The classical pathway is triggered by binding of pro-inflammatory cytokines (TNFα and IL-1) and of a number of pathogens to several different receptors in the TNF-receptor and Toll-like/IL-1 receptor superfamilies. This leads to recruitment to the plasma membrane and activation of the IκB-kinase complex (IKK) consisting of IKKα and IKKβ kinases, and the scaffold protein NEMO/IKKγ, as well as a number of IKK-associated proteins. The main NFκB that is activated in the classical pathway is the p50/p65 heterodimer that exists in the cytoplasm as a complex with inhibitory protein IκBα. Activation of IKK primarily through IKKβ results in phosphorylation of IκBα on Ser32 and Ser36, followed by polyubiquitination and degradation of IκBα by the 26S proteasome, allowing p50/p65 to translocate to the nucleus.

Release of p50/p65 from IκBα also can be achieved by IKK-independent pathways triggered by DNA damage or oxidative stress that result in phosphorylation of IκBα on Ser residues other than Ser32 or Ser36, again leading to proteosomal degradation of IκBα. This signaling pathway involves a number of kinases including the MAP kinase p38 and casein kinase 2. There is also an oxidative stress pathway that phosphorylates IκBα on Tyr residues, leading to release of p50/p65 without proteosomal degradation of IκBα. Superimposed on the complex activation of p50/p65 is additional downstream regulation of the DNA-binding properties of p50/p65 through phosphorylation, acetylation and peptidyl-prolyl isomerization. Mostly this occurs in p65 and provides multiple points for control of NF-κB activation in a cell-specific and environment-specific manner. A wide range of kinases can phosphorylate p50/p65, which appears essential for the transactivation potential of p50/p65. This includes phosphorylation at many different sites, especially in p65, which adds to the complex regulation of NF-κB.[4,10]

There are also alternative pathways to activation of NF-κB that result in formation of homo- or hetero-dimers other than p50/p65. A major alternative pathway, which is independent of IKKβ and NEMO, involves the IKKα homo-dimer whose activation is triggered by cytokines (other than TNFα), ligands such as CD40, and by certain viruses. This pathway requires recruitment of NF-κB-inducing kinase (NIK) with subsequent phosphorylation and activation of the IKKα homodimer. Activated IKKα phosphorylates p100, which is subsequently ubiquitinated and processed by the proteosome to p52. p52 and RelB then form a heterodimer that translocates to the nucleus. As with p50/p65, the p52/RelB heterodimer is further regulated by phosphorylation.[4]

A large number of compounds including natural products have been reported to inhibit activation of NF-κB at one or more sites in the complex pathways of activation.[11] This includes resveratrol (3,4',5-trihydroxystilbene, 1), a polyphenolic

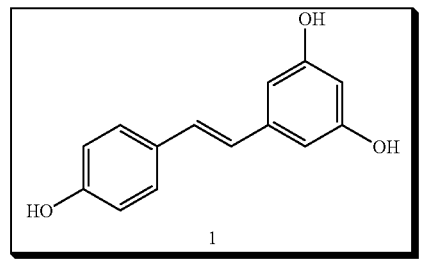 [SMILES: Oc1ccc(/C=C/c2cc(O)cc(O)c2)cc1]

phytochemical that is found in numerous foods and is especially abundant in red wine. It has been proposed that the anti-oxidant activity of resveratrol is responsible for the French Paradox;[12-14] this relates to the low incidence of cardiovascular disease in a French population with high intake of saturated fat.[15] Both trans and cis isomers of resveratrol occur as phytochemicals, and both possess biological activities. Most studies of the biological activities of resveratrol and of synthetic stilbene analogs of resveratrol have focused on trans isomers. Resveratrol has been studied extensively in the context of carcinogenesis as a chemoprevention agent. All three stages of carcinogenesis, i.e., initiation, promotion and progression, have been reported to be inhibited by resveratrol.[16] Because resveratrol exhibits anti-oxidant activity, which is based upon its phenolic groups, much of the research on resveratrol and on polyphenolic analogs of resveratrol has focused on anti-oxidant properties.[17-21] In addition, the multiple biological activities reported for resveratrol, which in addition to its cardio-protective and anti-carcinogenic activity also includes inhibition of platelet aggregation, modulation of lipoprotein metabolism, anti-inflammatory and vasorelaxing activities,[17,22-24] are often ascribed to the anti-oxidant properties of resveratrol. However, the oral bioavailability of resveratrol is low due to rapid metabolism, and the amount of resveratrol in dietary sources such as red wine is low compared to other polyphenols. Consequently, the circulating levels of resveratrol are low suggesting that the direct anti-oxidant effects of resveratrol are unlikely to explain its biological activities.[12] Therefore, there has been extensive interest in the ability of resveratrol and other plant polyphenols to affect signaling pathways, including NF-κB.[25] Signaling through NF-κB has been shown to be involved in the ability of resveratrol to induce heme oxygenase-1,[26] inhibit phorbol ester-induced expression of COX-2,[27] inhibit TNFα-induced proliferation of smooth muscle cells,[28] enhance the radiosensitivity of lung cancer cells,[29] and inhibit nitric oxide and TNFα production by LPS-activated microglia.[30]

Alzheimer's Disease

Alzheimer's disease (AD), the most common cause of dementia in elderly populations, currently afflicts almost 5 million people in the U.S., and this number is estimated to increase to 15 million by 2050. Most AD is sporadic with multiple risk factors, while some 10-15% is familial. It is well accepted that excessive production or diminished clearance of the Aβ peptide derived from the amyloid precursor protein (APP) is an essential factor in the etiology of AD. This is supported by studies of genetic mutations in APP in experimental animal models of AD as well as from studies of the genetics of familial AD.

There are two major neuropathological signatures of AD: extraneuronal amyloid plaques and neurofibrillary tangles. The plaques primarily consist of Aβ aggregates while the tangles consist of hyperphosphorylated tau protein. The exact mechanism by which these aggregates cause neuronal cell death remains to be established. However, considerable recent evidence points towards a major role for oligomeric forms of Aβ which are neurotoxic and can diffuse. Soluble Aβ is found in CSF of AD patients and correlates better with severity of disease than does the quantity of plaques. There are other common features of AD including the presence of chronic inflammation. The inflammatory response in brain is directed by activated microglia and reactive astrocytes. In normal brain, microglia are not activated. Under these conditions, neither pro-inflammatory signals nor reactive oxygen/nitrogen species (ROS/RNS) are formed. However, when microglia become activated in response to various insults, there is up-regulation of a number of surface receptors that promote phagocytotic activity by microglia. In addition, pro-inflammatory signals are released including interleukin-1β (IL1β) and tumor necrosis factor-α (TNFα) as well as ROS/RNS, thus contributing to the oxidative stress associated with AD. Activated microglia also associate with amyloid plaques. Microglia isolated from AD brain can scavenge Aβ. The considerable literature on the role of microglia in AD suggests that activation of microglia may contribute initially to clearance of Aβ aggregates, but that the chronic activation of microglia observed in AD leads to the neuropathological changes in the AD brain. Activated microglia also contribute to hyperphosphorylation of tau with development of neurofibrillary tangles, as well as to recruitment of activated astrocytes into the Aβ plaques.

It is now recognized that Aβ can increase the inflammatory response by activation of microglia and that the inflammatory response can contribute to Aβ deposition. Consequently there has been interest in hindering microglial activation as an approach to breaking this pathological cycle. Since activation of microglial results in release of ROS/RNS, attention has focused on use of anti-oxidants such as vitamin E. There are conflicting reports of the effects of anti-oxidants on development of AD, some supporting a role for anti-oxidants and others not supporting a role. Activation of microglia increases the oxidative burden in affected brain regions. However, how significant this increase is in contributing to neurodegeneration is not known. The field of anti-oxidant treatment of AD will need further controlled trials to assess this question.

Another area that has produced conflicting reports is the use of anti-inflammatory drugs, especially non-steroidal anti-inflammatory drugs (NSAIDS), in treatment of AD. COX-2, the inducible form of cyclooxygenase found in neurons and other cells and the source of pro-inflammatory eicosenoids, is up-regulated in AD brains. Overexpression of human COX-2 in mice results in age-related cognitive decline as well as neuronal apoptosis and astrocyte activation. The epidemiology studies of use of COX inhibitors (i.e. NSAIDs) by AD patients suggest that NSAID therapy may be useful. However, controlled clinical trials have been disappointing. These conflicting results may reflect the fact that the epidemiology studies begin with normal subjects and then assess risk of developing disease and whether this risk correlates inversely with drug use, whereas the clinical trials begin with subjects who have AD and look for improvement upon treatment. Other studies suggest that only a limited group of NSAIDs are effective and that these NSAIDs influence multiple targets in addition to COX-2. Animal model studies suggest that the dosing level of NSAID that is clinically feasible may not be sufficient to produce a pharmacological dose at the sites of plaque formation in AD brains.

Another area of interest in AD drug development focuses on signaling pathways that regulate expression of pro-inflammatory genes. Aβ stimulation of microglia results in up-regulation of the expression of TNFα and IL1 that is at least partly NFκB-dependent. IL1 is known to affect the expression of over 90 genes including those for cytokines, cytokine receptors, tissue remodeling enzymes and adhesion molecules. The mechanism for IL1 action involves activation of an IL1 receptor-mediated signal transduction pathway which leads to activation of NFκB. Thus NFκB is involved both in up-regulation of IL1 and in expression of the multiple genes regulated by IL1. These observations make inhibition of NFκB an attractive target for control of IL1-responsive genes in brain inflammation.

Diabetes

In 1998, it was suggested that the innate immune system is activated in diabetes, leading to a chronic inflammatory state that contributes to the disease process. More recently, there has been considerable support not only for an inflammatory contribution to diabetes but also to diabetic complications. Specifically, pro-inflammatory cytokines play a major role in microvascular complications. Endogenous production of TNF-α in vascular tissue is accelerated in diabetes where it contributes to increased vascular permeability in diabetic neuropathy. Both TNF-α and IL-1 expression are increased in diabetic retina where chronic low-grade inflammation appears to contribute to retinopathy. Likewise, diabetic nephropathy is associated with expression of inflammation markers such as CRP, fibrinogen and IL-6, and with increased expression of adhesion molecules such as ICAM-1, which promote inflammation by increasing leukocyte adherence and infiltration. The responses to these pro-inflammatory cytokines are especially prominent in endothelial cells (EC). Moreover, the response of EC to these cytokines commonly involves signaling through transcription factor NF-κB.

Oxidative stress has consistently been shown in experimental models of diabetes. Multiple mechanisms are involved that produce oxidative stress in EC in response to hyperglycemia, including: 1) protein glycosylation leading to AGE that trigger ROS production upon binding to the AGE receptor (RAGE); 2) glucose auto-oxidation; 3) accelerated metabolism of glucose through the aldose reductase/polyol pathway which consumes NADPH; 4) uncoupling of oxidative phosphorylation and of endothelial NO synthase (eNOS); 5) activation of specific isoforms of PKC; 6) increased flux through the hexosamine pathway; and 7) exposure to angiotensin II. Activation of NF-κB is often observed in response to these stresses. For example, exposure of EC to AGE generates ROS through activation of NADPH oxidase which then activates NF-κB followed by up-regulation of NF-κB-dependent cytokines and adhesion molecules. Angiotensin II can augment this process through crosstalk with the AGE-RAGE system, again involving NF-κB. High glucose can induce EC apoptosis through a PI-3-kinase-regulated expression of COX-2; this was shown to involve ROS and the NF-κB-regulated expression of COX-2. There has been considerable interest in a role for poly(ADP)-ribose polymerase (PARP) in EC dysfunction. PARP directly interacts with both the p50 and p65 subunits of NF-κB, suggesting that the role of PARP activation in diabetic complications is, at least in part, due to its interaction with NF-κB. Glucose-induced activation of NF-κB in EC is prevented by inhibitors of PKC, suggesting that the role of PKC in triggering the expression of pro-inflammatory cytokines is through downstream activation of NF-κB. There has also been considerable interest in mitochondria-derived ROS (specifically superoxide) produced in response to hyperglycemia and the relationship between these ROS and enhanced flux through the polyol pathway and the hexosamine pathway, PKC activation, and intracellular generation of AGE, all of which can be prevented by inhibiting the formation of mitochondria-derived ROS. The activation of these biochemical pathways appears to be due to ROS-induced activation of PARP, which results in inactivation of glyceraldehyde-3-phosphate dehydrogenase and subsequent accumulation of glycolytic intermediates that promote these pathways. It is noteworthy that inhibiting the production of mitochondria-derived ROS also prevents the activation of NF-κB, which may be related to the activation status of PARP. Clearly, activation of NF-κB appears to be a general feature of EC that are stressed by factors related to diabetic complications, suggesting a central role for NF-κB in EC dysfunction, especially as the key regulator of pro-inflammatory cytokines, adhesion molecules and extracellular matrix components, all of which are major players in diabetic microvascular complications.

The signaling mechanisms involved in inflammation that contributes to diabetes are under investigation, and are described by Wellen et al. (Wellen et al., J. Clin. Invest., 115, 1111-1119). This research indicates that inflammatory signaling pathways can be activated by metabolic stress or extracellular signaling molecules, and that endoplasmic reticulum stress (ER stress) leads to the activation of inflammatory signaling pathways and thus contributes to insulin resistance. Ozcan et al., Science, 306, 457-461 (2004). For example, several serine/threonine kinases are activated by inflammatory or stressful stimuli that contribute to inhibition of insulin signaling, including c-Jun N-terminal kinase (JNK) and I-κB kinase (IKK). The three members of the JNK group of kinases (JNK-1, -2, and -3) belong to the MAPK family and regulate multiple activities, in part through their ability to control transcription by phosphorylating activator protein-1 (AP-1). Loss of JNK1 has been shown to prevent the development of insulin resistance and diabetes in both genetic and dietary models of obesity.

A model of the overlapping metabolic and inflammatory signaling and sensing pathways in adipocytes and macrophages that influence diabetes and inflammation is provided by FIG. 2. As shown in FIG. 2, signals from various mediators converge on the inflammatory signaling pathways, including the kinases JNK and IKK. These pathways lead to the production of additional inflammatory mediators such as NF-κB and AP-1 through transcriptional regulation as well as to the direct inhibition of insulin signaling. Opposing the inflammatory pathways are transcriptional factors from the PPAR and LXR families, which promote nutrient transport and metabolism and antagonize inflammatory activity.

SUMMARY OF THE INVENTION

Figure 1:
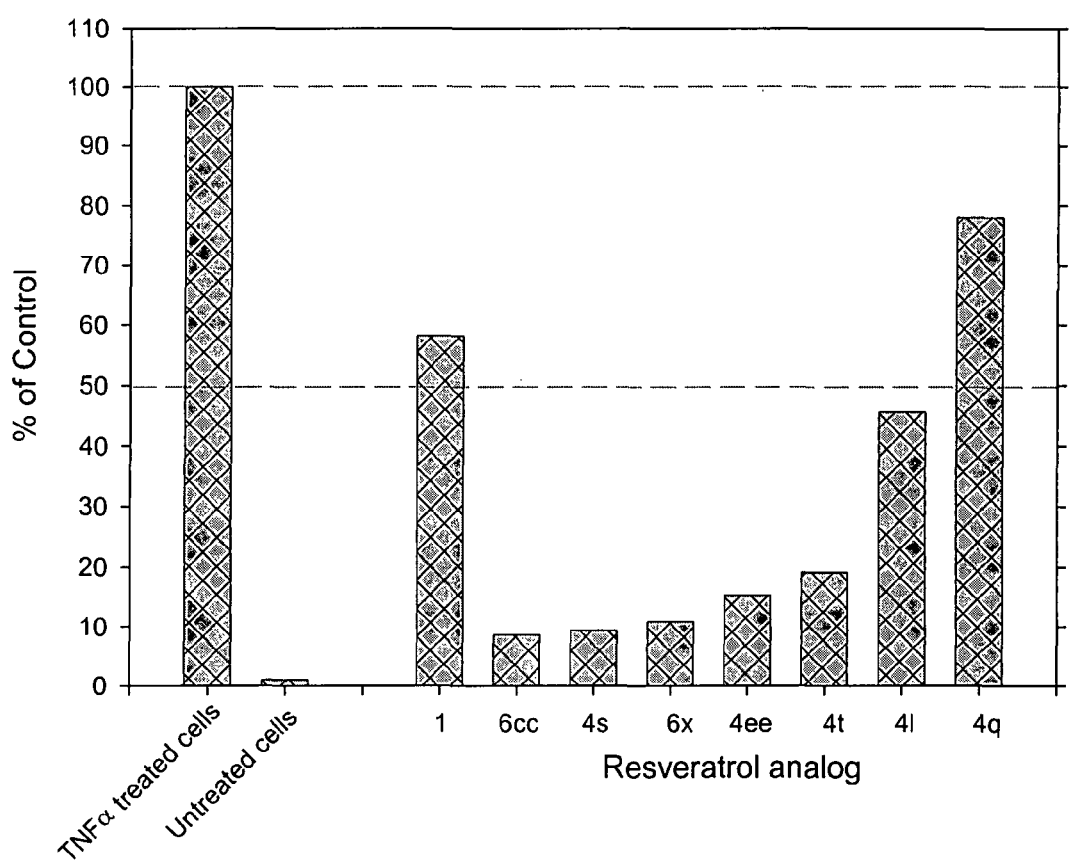
FIG. 1 shows the inhibition of the TNFα-induced activation of NF-κB by resveratrol (1) and analogs of resveratrol (Scheme 1). All of the resveratrol analogs retained anti-oxidant activity.

The present invention provides a method of a treating a subject afflicted with cancer or a precancerous condition, and/or an inflammatory disease or condition such as diabetes or Alzheimer's disease, or stroke or other ischemic disease or condition. The method includes administering to the subject a therapeutically effective amount of a cis- or trans-stilbene, preferably a substituted cis or trans-stilbene, more preferably an analog of the natural product resveratrol. Preferably, the compound that is administered in accordance with the treatment method of the invention is a small molecule inhibitor of NF-κB and/or AP-1. The composition optionally includes a pharmaceutically acceptable carrier. In some embodiments, the composition inhibits NF-κB or AP-1 activity in effecting a therapeutic result. In some aspects of the invention methods of reducing the likelihood of a disease or condition as otherwise described herein comprise administering to a subject or patient at risk for a disease or condition an effective amount of a compound as otherwise disclosed herein.

The present method relates to a method for treating or reducing the likelihood of cancer or a precancerous condition, and/or an inflammatory disease or condition such as diabetes or Alzheimer's disease, or stroke or other ischemic disease or condition in a subject or patient in need thereof comprising administering an effective amount of a cis- or trans-stilbene compound according to the general chemical structure (this structure represents both the cis- and trans-stilbene structures):

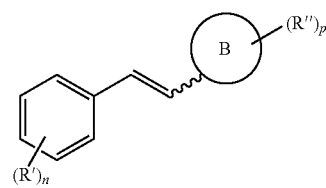

Where each R' is independently H, OH, halogen (F, Cl, Br, I), an optionally substituted —$(CH_2)_m XR$, —$(CH_2)_m R$ or —$(CH_2)_m C(O)R^3$ group, an optionally substituted $C_1$-$C_6$ (preferably, $C_1$-$C_3$) alkyl group, —CN, $NO_2$, a —$(CH_2)_m$ $NR^1R^2$ group, a —$(CH_2)_mC(O)NR^1R^2$ group or a —$(CH_2)_m OC(O)NR^1R^2$ group;

R is an optionally substituted $C_1$-$C_6$ hydrocarbyl group (preferably a $C_1$-$C_3$ optionally substituted alkyl group), an optionally substituted heterocylic group, an optionally substituted heteroaryl group or an optionally substituted $C_2$-$C_6$ acyl group;

$R^1$ and $R^2$ are each independently H or an optionally substituted $C_1$-$C_6$ hydrocarbyl (preferably a $C_1$-$C_3$ alkyl) group;

$R^3$ is H, OH or an optionally substituted —O—($C_1$-$C_6$)hydrocarbyl (preferably a $C_1$-$C_3$ alkyl) group, an optionally substituted heterocyclic group or an optionally substituted heteroaryl group;

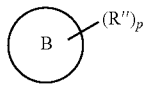

is an optionally substituted aryl or heteroaryl group wherein each R" is independently H, OH, halogen (F, Cl, Br, I), an optionally substituted —$(CH_2)_mXR$, —$(CH_2)_mR^a$ or —$(CH_2)_mC(O)R^{3a}$ group, an optionally substituted $C_1$-$C_6$ hydrocarbyl group, (preferably, a $C_1$-$C_3$ alkyl group), —CN, $NO_2$, a —$(CH_2)_mNR^{1a}R^{2a}$ group, a —$(CH_2)_mC(O)NR^{1a}R^{2a}$ group or a —$(CH_2)_mOC(O)NR^{1a}R^{2a}$ group;

Where $R^a$ is an optionally substituted $C_1$-$C_6$ hydrocarbyl group (preferably a $C_1$-$C_3$ optionally substituted alkyl group), an optionally substituted heterocyclic group, an optionally substituted heteroaryl group or an optionally substituted $C_2$-$C_6$ acyl group;

$R^{1a}$ and $R^{2a}$ are each independently H or an optionally substituted $C_1$-$C_6$ hydrocarbyl (preferably a $C_1$-$C_3$ alkyl) group; and $R^{3a}$ is H, OH, or an optionally substituted —$(CH_2)_m$—O—($C_1$-$C_6$) hydrocarbyl (preferably a $C_1$-$C_3$ alkyl) group, an optionally substituted heterocyclic group or an optionally substituted heteroaryl group;

X is O or S (preferably O);

m is an integer from 0-6, preferably 0-3;

n is an integer from 0-3;

p is an integer from 0-3, or a pharmaceutically acceptable salt, hydrate or solvate thereof.

Another aspect of the invention relates to compounds which are disclosed hereinabove. In another aspect of the invention, pharmaceutical compositions comprise an effective amount of a compound according to the present invention, optionally in combination with a pharmaceutically acceptable carrier, additive or excipient.

In another aspect, the present invention provides a method for identifying an antitumor or antiinflammatory substituted cis or trans-stilbene. The method includes contacting a cell that contains activatable NF-κB or AP-1 with a substituted cis- or trans-stilbene; contacting the cell with an NF-κB or AP-1 activator; and determining the effect on NF-κB or AP-1 activation by the substituted cis or trans-stilbene wherein a substituted cis- or trans-stilbene that reduces NF-κB or AP-1 activation is identified. In some embodiments of this aspect of the invention, the NF-κB or AP-1 activator may include TNF-α or IL-1. The cell can be, for example, a cancer cell.

Other methods involving the use of a substituted cis- or trans-stilbene, including methods of treatment and methods of identifying substituted cis- or trans-stilbenes that are effective to treat the diseases and conditions identified herein and in the cited references, are found in the following examples.

The compounds and methods of the invention are useful for treating or reducing the likelihood of any disease or condition characterized by inflammation, including Alzheimer's disease, diabetes (particularly type 2 diabetes), cancer or a precancerous condition (e.g., dysplasia or hyperplasia), cystic fibrosis, rheumatoid arthritis, asthma, inflammatory bowel disease, ulcerative colitis, atherosclerosis and stroke. A subject afflicted with diabetes who is treated in accordance with the invention may exhibit endothelial dysfunction by one or more endothelial cells that express activated NF-κB or AP-1. It should be understood that the method of the invention is generally useful for treating any disease or condition that can be ameliorated by inhibiting or otherwise modulating the activity of NFkB or AP-1.

The compounds according to the present invention can be used to inhibit or otherwise modulate the activity of NFkB or AP-1. Compounds according to the present invention have antagonist and/or agonist activity against these receptors. Compounds according to the present invention can be used to treat a number of disease states which are mediated through these receptors.

In some embodiments of the method of treating a subject with Alzheimer's disease or decreasing the likelihood of Alzheimer's disease in a subject or patient, the composition inhibits amyloid plaque formation. In other embodiments, the composition inhibits aggregation of a plurality of Aβ peptides. In additional embodiments, the composition inhibits oligomerization of a plurality of Aβ peptides. In further embodiments, the composition decreases the cytotoxicity of an Aβ peptide aggregate. In yet further embodiments, the composition decreases activation of a glial cell by an Aβ peptide aggregate.

The cis- or trans-stilbene compounds provided herein optionally inhibit the activity of AP-1 or NF-κB. Inhibition of activity may be observed or demonstrated by in vitro assays, in vivo, or both. Inhibition of activity may decrease inflammation, insulin resistance and/or render a cancer cell more susceptible to a chemotherapeutic agent.

In embodiments of the invention that involve the treatment of cancer or a precancerous condition, the cis- or trans-stilbene may be administered to the subject either alone or in combination with one or more other cancer drugs (e.g., chemotherapeutic agents), for example in an assistive or adjuvant capacity. The cis- or trans-stilbene compound may be administered before, concurrent with, or after the administration of the other cancer drug(s).

In another aspect, the present invention provides methods for identifying a therapeutic cis or trans-stilbene compound that includes contacting a cell containing NF-κB or AP-1 with a cis- or trans-stilbene, contacting the cell with an activator of NF-κB or AP-1 and determining the effect of the cis or trans-stilbene on cell activation by the activator, wherein a cis- or trans-stilbene that reduces cell activation is identified as a therapeutic stilbene derivative. Exemplary activators include TNF-α or IL-1. In a further embodiment, the cell is an adipocyte or endothelial cell.

In another aspect, the invention provides a method for identifying a therapeutic cis- or trans-stilbene compound that includes contacting a brain cell comprising an inflammation activator with a stilbene derivative and determining the effect of the compound on activation of the brain cell by the inflammation activator. A cis- or trans-stilbene compound that reduces brain cell activation when tested by this method is identified as a therapeutic cis- or trans-stilbene compound. The inflammation activator of this method may include NF-κB or AP-1. In one or more embodiments, the brain cell is a glial cell.

In another aspect, the invention provides a method for identifying a therapeutic cis- or trans-stilbene compound that includes contacting a solution including an Aβ peptide with a stilbene derivative and determining the effect of the cis- or trans-stilbene compound on aggregation by the Aβ peptide. A cis- or trans-stilbene compound that reduces aggregation of the Aβ peptide is identified as a therapeutic cis- or trans-stilbene compound. In one ore more embodiments, effect of the cis- or trans-stilbene compound on aggregation by the Aβ peptide is determined by an immunological assay.

DETAILED DESCRIPTION OF THE INVENTION

Unless otherwise specified, "a," "an," "the," and "at least one" are used interchangeably and mean one or more than one.

The following terms shall be used to describe the present invention. In instances where a term is not defined herein, such term is given its common meaning by those of ordinary skill in the art.

The term "patient" or "subject" refers to a mammal, preferably a human, in need of treatment or therapy to which compounds according to the present invention are administered in order to treat a condition or disease state otherwise described herein.

The term "compound", as used herein, unless otherwise indicated, refers to any specific chemical compound disclosed herein and includes in context, tautomers, regioisomers (especially cis/trans- see below), geometric isomers, and where applicable, optical isomers thereof, as well as pharmaceutically acceptable salts, solvates and polymorphs thereof. Within its use in context, the term compound generally refers to a single compound, but also may include other compounds such as stereoisomers, regioisomers and/or optical isomers (including in some instances, racemic mixtures) as well as specific enantiomers or enantiomerically enriched mixtures of disclosed compounds. The compounds of this invention include all stereoisomers where relevant (e.g., both cis and trans isomers—as represented by a ~~~ bond) and all optical isomers of the present compounds (eg., R and S enantiomers), as well as racemic, diastereomeric and/or other mixtures of such isomers, as well as all pharmaceutically acceptable salt forms, solvates, polymorphs and prodrug forms of the present compounds, where applicable. The present invention relates both the cis- and trans-stilbene structures as generally presented below and their methods of use.

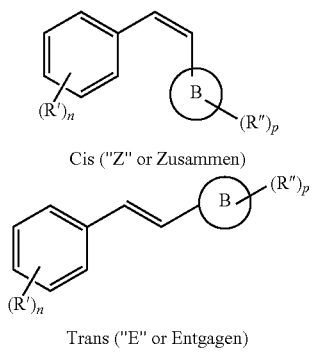

Cis ("Z" or Zusammen)

Trans ("E" or Entgagen)

The term "modulate" means, with respect to disease states or conditions, modulated through (e.g, by binding) or having an effect on NF-κB or AP-1 to produce, either directly or indirectly, an improvement or lessening of a condition or disease state which was, prior to administration of a compound according to the present invention, sub-optimal and in many cases, debilitating and even life threatening. Modulation may occur by virtue of agonist activity, antagonist activity or mixed agonist/antagonist activity (depending on the receptor site). In most/many instances, the term modulate shall mean direct or indirect inhibition of NF-κB or AP-1 alone or within the context of treating a disease or condition associated with same.

The term "independently" is used herein to indicate that the variable, which is independently applied, varies independently from application to application.

The term "non-existent" or "absent" refers to the fact that a substituent is absent and the group to which such substituent is attached forms an additional bond with an adjacent atom or group.

The term "optionally substituted" means optional substitution with the specified groups, radicals or moieties. It should be noted that any atom with unsatisfied valences in the text, schemes, examples and tables herein is assumed to have the hydrogen atom(s) to satisfy the valences.

The term "cancer" includes any cancer of any origin and is used to describe all cancerous disease states and embraces or encompasses the pathological process associated with malignant hematogenous, ascitic, and solid tumors. The term "cancer" and the term "tumor" used in this application is interchangeable with the term "neoplasia".

Cancer which may be treated using compositions according to the present invention include, for example, cancers of the stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, melanoma, acute leukemia, including lymphocytic leukemia, hairy cell leukemia, and acute myelogenous leukemia, Ewing's sarcoma, small cell lung cancer, choriocarcinoma, rhabdomyosarcoma, Wilms' Tumor, neuroblastoma, mouth/pharynx, oesophagus, larynx, kidney, lymphoma, among others, and in particular, breast; reproductive, ovarian, cervical, uterine, endometrial and other hormone-dependent cancers. Drug-resistant cancers are also treatable using compounds according to the present invention and represent a preferred embodiment of the present invention.

The term "anti-cancer compound" or "anti-cancer agent" is used to describe any compound (including its derivatives) which may be used to treat cancer and is used in combination with one or more of the compounds according to the present invention in the treatment of cancer. The term "second anti-cancer compound" or "second anti-cancer agent" may also apply to these agents in context. Anti-cancer agents as described hereunder are a subset of cytotoxic agents which may be used in the present invention in coadministration with compounds according to the present invention. Exemplary anti-cancer compounds for use in the present invention include anti-metabolite agents which are broadly characterized as antimetabolites, inhibitors of topoisomerase I and II, alkylating agents and microtubule inhibitors (e.g., taxol), as well as tyrosine kinase inhibitors (e.g., surafenib), EGF kinase inhibitors (e.g., tarceva or erlotinib) and ABL kinase inhibitors (e.g. gleevec or imatinib). Anti-cancer compounds for use in the present invention include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin;

cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin: mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others. Note that one of ordinary skill in the art may readily employ any one or more of these second anti-cancer agents in combination with compounds according to the present invention to treat cancer.

The term "ischemia" is used to describe a condition in which the blood flow (and thus oxygen) is restricted to a part of the body. Cardiac ischemia is the name for lack of blood flow and oxygen to the heart muscle. Ishchemia includes stroke.

The term "stroke" is used to describe a brain attack, which is a major cause of death and permanent disability. They occur when blood flow to a region of the brain is obstructed and may result in death of brain tissue.

There are two main types of stroke: ischemic and hemorrhagic. Ischemic stroke is caused by blockage in an artery that supplies blood to the brain, resulting in a deficiency in blood flow (ischemia). Hemorrhagic stroke is caused by the bleeding of ruptured blood vessels (hemorrhage) in the brain. During ischemic stroke, diminished blood flow initiates a series of events (called ischemic cascade) that may result in additional, delayed damage to brain cells. Early medical intervention can halt this process and reduce the risk for irreversible complications.

Strokes, or brain attacks, are medical emergencies that require immediate medical attention. Warning signs of stroke include the following:
  Sudden numbness or weakness, especially on one side of the body
  Sudden confusion
  Sudden vision problems in one or both eyes
  Sudden difficulty walking, dizziness, loss of balance or coordination
  Sudden, severe headache with no known cause
  Sudden difficulty speaking or understanding speech.

The term "hydrocarbyl" refers to any radical containing carbon and hydrogen, which may be straight, branch-chained or cyclic in nature. Hydrocarbons include linear, branched and cyclic hydrocarbons, including alkyl groups, alkylene groups and unsaturated hydrocarbon groups, which may be optionally substituted. Hydrocarbyl groups may be fully saturated or unsaturated, containing one or more double ("ene") or triple ("yne") bonds.

"Alkyl" refers to a fully saturated monovalent hydrocarbyl radical containing carbon and hydrogen, and which may be cyclic, branched or a straight chain. Examples of alkyl groups are methyl, ethyl, n-butyl, n-hexyl, n-heptyl, n-octyl, isopropyl, 2-methylpropyl, cyclopropyl, cyclopropylmethyl, cyclobutyl, cyclopentyl, cyclopentylethyl, cyclohexylethyl and cyclohexyl. Preferred alkyl groups are $C_1$-$C_6$ alkyl groups.

"Alkylene" refers to a fully saturated hydrocarbon which is divalent (may be linear, branched or cyclic) and which is optionally substituted. Other terms used to indicate substituent groups in compounds according to the present invention are as conventionally used in the art. Thus, the term alkylene aryl includes alkylene phenyl such as a benzyl group or ethylene phenyl group, alkylaryl, includes alkylphenyl such a phenyl group which has alkyl groups as substituents, etc.

"Aryl" refers to a substituted or unsubstituted monovalent aromatic radical having a single ring (e.g., phenyl) or multiple condensed rings (e.g., naphthyl, anthracenyl, phenanthryl) and can be can be bound to compound according to the present invention at any position on the ring(s).

The term "heteroaryl" refers to an optionally substituted (at varying positions as appropriate within context) heterocyclic aromatic ring system having one or more nitrogen, oxygen, or sulfur atoms in the ring, such as imidazolyl, furyl, thiophene (thienyl), pyrrole, pyridine, pyrimidinyl, quinoline, isoquinoline, indole, isoindole, triazole, tetrazole, pyrazolyl, oxazolyl, thiazolyl, benzofuranyl, benzothiophenyl, carbazolyl, benzoxazolyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, among numerous others. Monocyclic and fused ring systems are contemplated for use in the present invention.

The term "heterocycle" or "heterocyclic" shall mean an optionally substituted moiety which is cyclic and contains at least one atom other than a carbon atom, such as a nitrogen, sulfur, oxygen or other atom. A heterocyclic ring shall contain up to four atoms other than carbon selected from nitrogen, sulfur and oxygen. These rings may be saturated or have unsaturated bonds. Fused rings are also contemplated by the present invention. A heterocycle according to the present invention is an imidazole, a piperazine, piperidine, furan, pyrrole, imidazole, thiazole, oxazole or isoxazole group, all optionally substituted, among numerous others, including those groups described as heteroaryl groups hereunder. Depending upon its use in context, a heterocyclic ring may be saturated and/or unsaturated. In instances where a heterocyclic ring is fully unsaturated, there is overlap with the term "heteroaryl".

"Alkoxy" as used herein refers to an alkyl group bound through an ether linkage; that is, an "alkoxy" group may be represented as —O-alkyl where alkyl is as defined above.

The term "cyclic" shall refer to a carbocyclic or heterocyclic group, preferably a 5- or 6-membered ring, but may include 4 and 7-membered rings, but may, in context, refer to a group with two or more fused rings.

The term "unsubstituted" shall mean substituted only with hydrogen atoms. The term "substituted" shall mean, within the chemical context of the compound defined, a substituent (each of which substituents may itself be substituted) selected from a hydrocarbyl (which may be substituted itself, preferably with an optionally substituted alkyl or halogen (fluoro) group, among others), preferably an alkyl (generally, no greater than about 12 carbon units in length), an optionally substituted aryl (which also may be heteroaryl and may include an alkylenearyl or alkyleneheteroaryl), an optionally substituted heterocycle (especially including an alkyleneheterocycle), $CF_3$, halogen (especially fluoro), thiol, hydroxyl, carboxyl, oxygen (to form a keto group), $C_1$-$C_8$ alkoxy, $C_1$-$C_8$ alkoxyether, CN, nitro, an optionally substituted amine (e.g. an alkyleneamine or a $C_1$-$C_6$ monoalkyl or dialkyl amine), $C_1$-$C_8$ acyl, $C_1$-$C_8$ alkylester, $C_1$-$C_8$ alkyleneacyl (keto), $C_1$-$C_8$ alkylene ester, carboxylic acid, alkylene carboxylic acid, $C_1$-$C_8$ thioester, $C_2$-$C_8$ ether, $C_1$-$C_8$ mono- or dithioether, $C_1$-$C_8$ diether (alkoxyether), amide (amido or carboxamido), substituted amide (especially mono- or di-alkylamide) or alkyleneamide, an optionally substituted carbamate or urethane group, wherein an alkylene group or other carbon group not otherwise specified contains from 1 to 8 carbon units long (alternatively, about 2-6 carbon units long) and the alkyl group on an ester group is from 1 to 8 carbon units long, preferably up to 4 carbon units long. Various optionally substituted moieties may be substituted with 5 or more substituents, preferably no more than 3 substituents and preferably from 1 to 3 substituents.

The term "fused aryl ring" includes fused carbocyclic aromatic rings or ring systems. Examples of fused aryl rings include benzo, naphtho, fluoreno, and indeno.

The term "annulene" refers to aryl groups that are completely conjugated monocyclic hydrocarbons. Annulenes have a general formula of $C_nH_n$, where n is an even number, or $C_nH_{n+1}$, where n is an odd number. Examples of annulenes include cyclobutadiene, benzene, and cyclooctatetraene. Annulenes present in an aryl group will typically have one or more hydrogen atoms substituted with other atoms such as carbon.

When a group is present more than once in any formula or scheme described herein, each group (or substituent) is independently selected, whether explicitly stated or not. For example, for the formula —C(O)—$NR_2$ each of the two R groups is independently selected.

The term "geometric isomer" shall be used to signify an isomer of a compound according to the present invention wherein a chemical group or atom occupies different spatial positions in relation to double bonds or in saturated ring systems having at least three members in the ring as well as in certain coordination compounds. Thus "cis" and "trans" isomers are geometric isomers as well as isomers of for example, cyclohexane and other cyclic systems. In the present invention, the double bond between the aryl and aryl/heteroaryl (B) group is a trans double bond. In all other cases, a double bond may be cis or trans.

The term "coadministration" or "combination therapy" is used to describe a therapy in which at least two active compounds in effective amounts are used to treat cancer or another disease state or condition as otherwise described herein at the same time. Although the term coadministration preferably includes the administration of two active compounds to the patient at the same time, it is not necessary that the compounds be administered to the patient at the same time, although effective amounts of the individual compounds will be present in the patient at the same time. In cancer aspects of the invention, trans-stilbene compounds according to the present invention may be administered with one or more anti-cancer agent, including antimetabolites, alkylating agents, topoisomerase I and topoisomerase II inhibitors as well as microtubule inhibitors, among others. Anticancer compounds for use in the present invention include those described above, and mixtures thereof, among others. Coadministration of one of the present compounds with another anticancer agent as otherwise described herein will often result in a synergistic enhancement of the anticancer activity of the other anticancer agent, an unexpected result. One or more of the present compounds may also be coadministered with another bioactive agent (e.g., antiviral, agent, antihyperproliferative disease agent, agents which treat chronic inflammatory disease, among others or as otherwise described herein), depending upon the desired therapeutic outcome and the disease state or condition treated.

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc.

Treatment, as used herein, encompasses both prophylactic and therapeutic treatment. Cis- and trans-stilbene compounds of the invention can, for example, be administered prophylactically to a mammal in advance of the occurrence of disease. Prophylactic administration is effective to decrease the likelihood of the subsequent occurrence of disease in the mammal, or decrease the severity of disease that subsequently occurs. Alternatively, cis- and trans-stilbene compounds of the invention can, for example, be administered therapeutically to a mammal that is already afflicted by disease. In one embodiment of therapeutic administration, administration of the cis- and trans-stilbene compounds is effective to eliminate the disease; in another embodiment, administration of the cis- and trans-stilbene compounds is effective to decrease the severity of the disease or lengthen the lifespan of the mammal so afflicted.

"Pharmaceutically acceptable" as used herein means that the compound or composition is suitable for administration to a subject to achieve the treatments described herein, without unduly deleterious side effects in light of the severity of the disease and necessity of the treatment.

"Inhibit" as used herein refers to the partial or complete elimination of a potential effect, while inhibitors are compounds that have the ability to inhibit.

The present invention includes the compositions comprising the pharmaceutically acceptable salt. i.e., the acid or base addition salts of compounds of the present invention and their derivatives. The acids which may be used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among others.

Pharmaceutically acceptable base addition salts may also be used to produce pharmaceutically acceptable salt forms of the compounds according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (e, calcium and magnesium), ammonium or water-soluble amine addition salts such as N-methylglucamine-(meglumine), and the lower alkanolammonium and other base salts of pharmaceutically acceptable organic amines, among others.

Regardless of the mechanism, the compounds of the present invention may be used to treat disease states or conditions in patients or subjects who suffer from those conditions or disease states or are at risk for those conditions. In this method a compound in an effective amount is administered to a patient in need of therapy to treat or reduce the likelihood of the occurrence of the condition(s) or disease state(s). The compounds and methods of the invention are useful for treating or reducing the likelihood of any disease or condition characterized by inflammation, including Alzheimer's disease, diabetes (particularly type 2 diabetes), cancer or a precancerous condition (e.g., dysplasia or hyperplasia), cystic fibrosis, rheumatoid arthritis, asthma, inflammatory bowel disease, ulcerative colitis, atherosclerosis and stroke. A subject afflicted with diabetes who is treated in accordance with the invention may exhibit endothelial dysfunction by one or more endothelial cells that express activated NF-κB or AP-1. It should be understood that the method of the invention is generally useful for treating any disease or condition that can be ameliorated by inhibiting the activity of NFκB or AP-1.

Compositions according to the present invention may be administered by any conventional means known in the art. Pharmaceutical formulations include those suitable for oral, rectal, nasal, topical (including buccal and sub-lingual), vaginal or parenteral (including intramuscular, sub-cutaneous and intravenous) administration. Compositions according to the present invention may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. When desired, the above described formulations may be adapted to provide sustained release characteristics of the active ingredient(s) in the composition using standard methods well-known in the art.

In the pharmaceutical aspect according to the present invention, the compound(s) according to the present invention is formulated preferably in admixture with a pharmaceutically acceptable carrier. In general, it is preferable to administer the pharmaceutical composition orally, but certain formulations may be preferably administered parenterally and in particular, in intravenous or intramuscular dosage form, as well as via other parenteral routes, such as transdermal, buccal, subcutaneous, suppository or other route, including via inhalations intranasally. Oral dosage forms are preferably administered in tablet or capsule (preferably, hard or soft gelatin) form. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity.

Compositions suitable for parenteral injection may comprise physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants.

These compositions may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, sesame seed oil, glycerol, tetrahydrofurfuryl alcohol, polyethylene glycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

Compositions for rectal or vaginal administration, where applicable, can be prepared by mixing an active agent and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the active.

Dosage forms for topical administration include ointments, powders, sprays and inhalants. The compound(s) are admixed under sterile conditions with a physiologically acceptable carrier, and any preservatives, buffers, and/or propellants that may be required. Opthalmic formulations, eye ointments, powders, and solutions are also contemplated as being within the scope of this invention.

Disease Treatment using the Present Compounds

Treatment, as defined herein, is the amelioration of the symptoms associated with disease. Symptoms may be reduced either by decreasing the level of the disease itself, or by decreasing the symptoms associated with the disease. The subject of the treatment is preferably a mammal, such as a domesticated farm animal (e.g., cow, horse, pig) or pet (e.g., dog, cat). More preferably, the subject is a human.

As noted herein, and without being bound by any particular theory, one mechanism by which administration of the cis or trans-stilbene compounds according to the present invention may treat disease is through inhibition of the activity of AP-1 or NF-κB. Inhibition of NF-κB results in a decrease in NF-κB activity, and includes direct inhibition and indirect inhibition. Direct inhibition is the direct effect of a cis or trans-stilbene compound on NF-κB and its activity. For example, one type of direct inhibition of NF-κB is a block of NF-κB DNA interactions. Indirect inhibition, on the other hand, involves the effect of a cis or trans-stilbene on other compounds involved in the regulation of NF-κB that leads to a decrease in NF-κB activity. For example, as phosphorylation of the NF-κB regulator IκB by IκB kinases (IKK) or Src family kinases (SFK) results in a dysregulation of NF-κB, and an according increase in NF-κB activity, inhibition of IKK or SFK by cis- or trans-stilbene compounds provides an example of indirect inhibition.

Inhibition of AP-1 results in a decrease in AP-1 activity, and includes direct inhibition and indirect inhibition. Direct inhibition is the direct effect of a cis or trans-stilbene compound on AP-1 (or its subunits) and its activity. Indirect inhibition, on the other hand, involves the effect of a cis- or trans-stilbene compounds or other compound in the regulation of AP-1 that leads to a decrease in AP-1 activity. For example, indirect inhibition of AP-1 activity may occur as a result of an affect on AP-1 activating proteins such as mitogen-activated protein kinases (MAPK) or c-Fos-regulating kinase (FRK).

Alzheimer's Disease

In one aspect, the present invention provides a method of using cis- or trans-stilbene compounds according to the present invention to treat a subject with Alzheimer's disease. The present invention also provides a method of the present compounds to treat symptoms of Alzheimer's disease in a subject with Alzheimer's disease. The present compounds treat Alzheimer's disease through one or more biochemical mechanisms. For example, without being bound by theory, administration of the present compounds may treat Alzheimer's disease by inhibiting the activity of AP-1 and/or NF-κB. Decreasing the activity of AP-1 and/or NF-κB may, in turn, lead to a decrease in inflammation.

As another example, again without being bound by theory, administration of the present compounds may treat Alzheimer's disease through an effect on the Aβ peptide, for example by inhibiting the formation of Aβ oligomers and fibrils, reducing Aβ peptide aggregation, or by reducing the Aβ amyloid burden of subjects with Alzheimer's disease (see Riviere et al, *Bioorganic Medicinal Chemistry* 15 (2007) 1160-1167). The effects of the present compounds on Aβ peptide aggregation may include binding to Aβ peptide aggregates and/or effects on Aβ peptide conformation. Effects on Aβ peptide conformation include destabilization of the β-sheet conformation of Aβ peptide aggregates, and/or the stabilization of non-aggregated Aβ peptide α-helical/random coil conformation. The effects of cis- or trans-stilbene compounds may further include a decrease in the cytotoxicity of Aβ peptide aggregates, or a decrease in glial cell activation by Aβ peptide aggregates.

Symptoms of Alzheimer's disease include, for example, formation of amyloid plaques and neurofibrillary tangles, chronic brain inflammation, glial cell activation, and cognitive decline. A number of other symptoms are known and can be readily identified by one skilled in the art.

Type 2 Diabetes

In another aspect, the present invention provides a method of using trans-stilbene compounds to treat a subject with type 2 diabetes. The present invention also provides a method of using cis or trans-stilbene compounds to treat symptoms of diabetes in a subject with type 2 diabetes such as inflammation or insulin resistance.

Symptoms of type 2 diabetes include, for example, insulin resistance and inflammation. A number of other symptoms are known and can be readily identified by one skilled in the art.

Other Inflammatory Diseases or Conditions

The present invention provides a method of using compounds according to the present invention to treat a subject with any disease or condition characterized by inflammation, including Alzheimer's disease, diabetes (particularly type 2 diabetes), cancer, cystic fibrosis, rheumatoid arthritis, asthma, inflammatory bowel disease, ulcerative colitis, atherosclerosis and stroke.

Assistive or Adjuvant Treatment for Cancer

In another aspect, the present invention pertains generally to treatment of cancer or a precancerous condition such as dysplasia or hyperplasia, by administering a cis or trans-stilbene compound of the invention. Administration of a compound according to the present invention may advantageously inhibit the activity of NFκB and/or AP-1.

In a preferred embodiment, administration of the cis or trans-stilbene compound is effected in combination (coadministration) with the administration of another chemotherapeutic agent. The cis or trans-stilbene compounds can be administered before, during of after the administration of the chemotherapeutic agent. Administration of thecis or trans-stilbene compound is especially advantageous in cases where the cancer cells may develop or have developed resistance to the chemotherapeutic agent.

Chemistry

Trans-stilbenes

The synthesis of a library of 75 (E)-stilbenes was accomplished as shown in Schemes 1, 2 and 3. Initially our strategy for the construction of the trans-stilbene skeleton involved the reaction of an aromatic phosphonium ylide with substituted benzaldehydes.[31] This method proved to be unsatisfactory due to the formation of a mixture of E and Z isomers and the formation of triphenylphosphine oxide, which complicates the purification process. It is known that semi-stabilized ylides such as benzyl ylides give mixtures of isomers, which can be converted to E isomers by heating with a catalytic amount of iodine in heptane or toluene. In order to avoid these problems, Homer-Emmons-Wadsworth olefination chemistry was utilized as described by Lion et al.[32] Reaction of benzylphosphonic acid diethyl ester (2) with substituted benzaldehydes (3a-3k, 3m-3p, 3r, 3u-3dd, 3ff, 3gg) or methoxymethyl (MOM) hydroxyl substituted benzaldehydes (3hh-3ll) in DMF using sodium methoxide as the base in the presence of 18-crown-6 at 120° C. afforded 33 substituted stilbenes or methoxymethyl hydroxystilbenes (4) exclusively in the (E)-conformation (Scheme 1). There was no detectable Z isomer by $^1$H NMR analysis. The diethylphosphoric acid byproduct is water soluble and was easily removed. In the case of the MOM protected benzaldehydes, (4hh-4ll), which were stable under the Horner-Emmons-Wadsworth conditions, the methoxymethyl protecting group was readily removed in a second step using hydrochloric acid to give the phenolic stilbene Emmons-Wadsworth conditions afforded 31 trans-stilbenes (6) having one anisole ring as shown in Scheme 2. The methoxymethyl protecting group on compounds 6ff and 6gg was readily removed using hydrochloric acid to give 6x and 6cc.

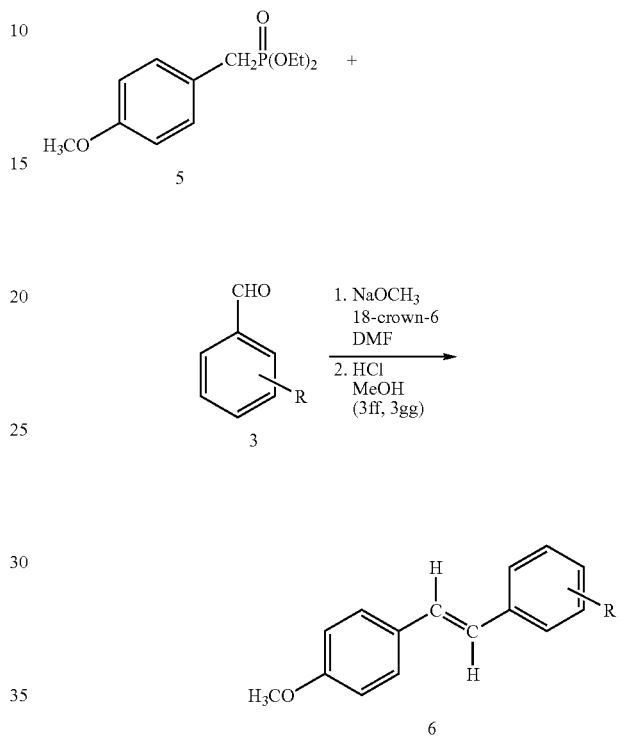

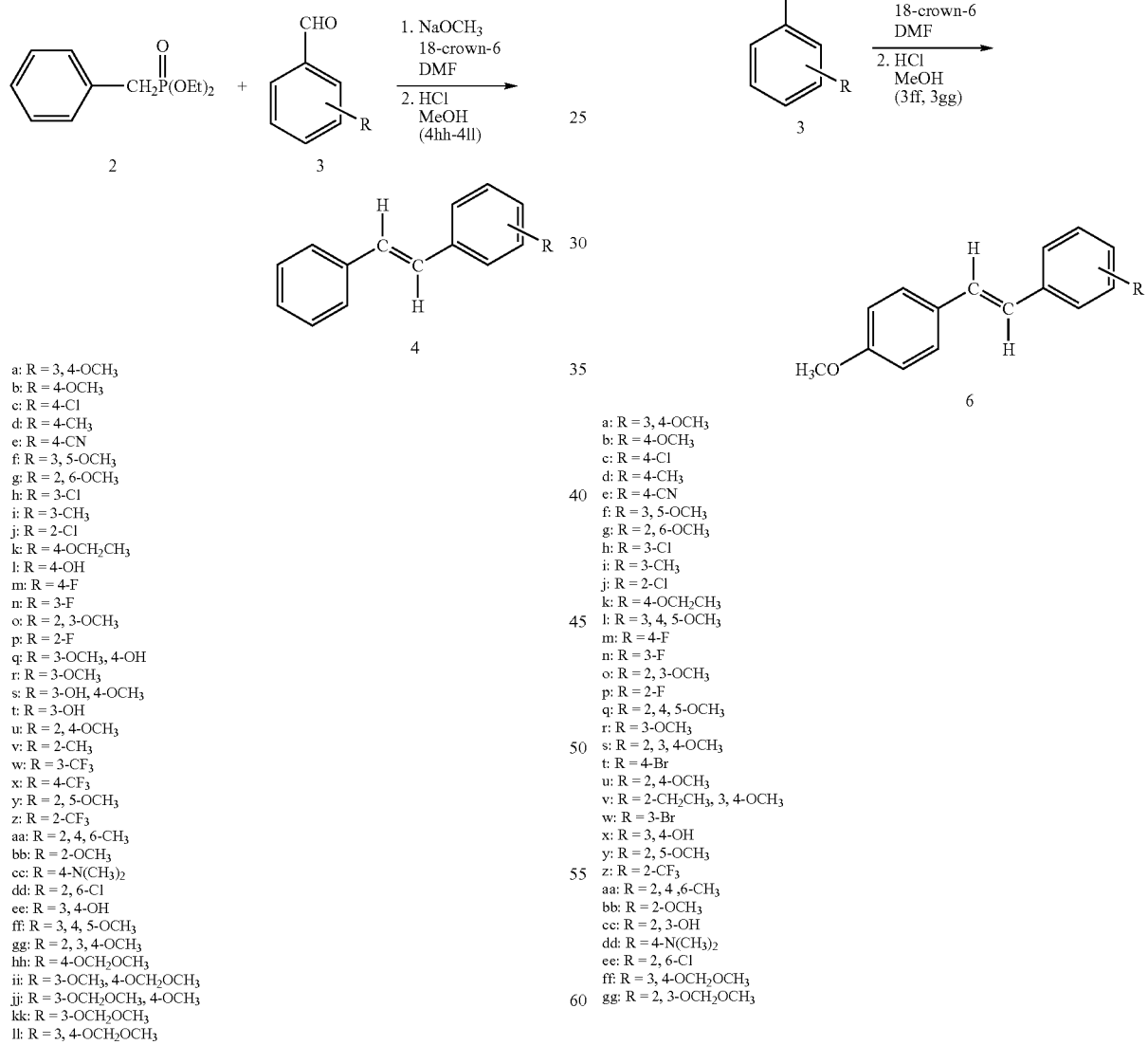

a: R = 3, 4-OCH$_3$
b: R = 4-OCH$_3$
c: R = 4-Cl
d: R = 4-CH$_3$
e: R = 4-CN
f: R = 3, 5-OCH$_3$
g: R = 2, 6-OCH$_3$
h: R = 3-Cl
i: R = 3-CH$_3$
j: R = 2-Cl
k: R = 4-OCH$_2$CH$_3$
l: R = 4-OH
m: R = 4-F
n: R = 3-F
o: R = 2, 3-OCH$_3$
p: R = 2-F
q: R = 3-OCH$_3$, 4-OH
r: R = 3-OCH$_3$
s: R = 3-OH, 4-OCH$_3$
t: R = 3-OH
u: R = 2, 4-OCH$_3$
v: R = 2-CH$_3$
w: R = 3-CF$_3$
x: R = 4-CF$_3$
y: R = 2, 5-OCH$_3$
z: R = 2-CF$_3$
aa: R = 2, 4, 6-CH$_3$
bb: R = 2-OCH$_3$
cc: R = 4-N(CH$_3$)$_2$
dd: R = 2, 6-Cl
ee: R = 3, 4-OH
ff: R = 3, 4, 5-OCH$_3$
gg: R = 2, 3, 4-OCH$_3$
hh: R = 4-OCH$_2$OCH$_3$
ii: R = 3-OCH$_3$, 4-OCH$_2$OCH$_3$
jj: R = 3-OCH$_2$OCH$_3$, 4-OCH$_3$
kk: R = 3-OCH$_2$OCH$_3$
ll: R = 3, 4-OCH$_2$OCH$_3$ a: R = 3, 4-OCH$_3$
b: R = 4-OCH$_3$
c: R = 4-Cl
d: R = 4-CH$_3$
e: R = 4-CN
f: R = 3, 5-OCH$_3$
g: R = 2, 6-OCH$_3$
h: R = 3-Cl
i: R = 3-CH$_3$
j: R = 2-Cl
k: R = 4-OCH$_2$CH$_3$
l: R = 3, 4, 5-OCH$_3$
m: R = 4-F
n: R = 3-F
o: R = 2, 3-OCH$_3$
p: R = 2-F
q: R = 2, 4, 5-OCH$_3$
r: R = 3-OCH$_3$
s: R = 2, 3, 4-OCH$_3$
t: R = 4-Br
u: R = 2, 4-OCH$_3$
v: R = 2-CH$_2$CH$_3$, 3, 4-OCH$_3$
w: R = 3-Br
x: R = 3, 4-OH
y: R = 2, 5-OCH$_3$
z: R = 2-CF$_3$
aa: R = 2, 4 ,6-CH$_3$
bb: R = 2-OCH$_3$
cc: R = 2, 3-OH
dd: R = 4-N(CH$_3$)$_2$
ee: R = 2, 6-Cl
ff: R = 3, 4-OCH$_2$OCH$_3$
gg: R = 2, 3-OCH$_2$OCH$_3$

Reaction of p-methoxybenzylphosphonic acid diethyl ester (5) with the appropriately substituted benzaldehydes (3a-3w, 3y-3bb, 3dd, 3ee) or methoxymethyl hydroxyl substituted benzaldehydes (3ff, 3gg) under the same Horner- Scheme 3, below, shows the reaction of benzyl- or p-methoxybenzyl-phosphonic acid diethyl esters (2 or 5) with pyridyl, thienyl and naphthyl aldehydes (7) under Horner-Emmons-Wadsworth conditions to afford 10 pyridyl, thienyl and naphthyl trans-stilbenes (8).

Scheme 3

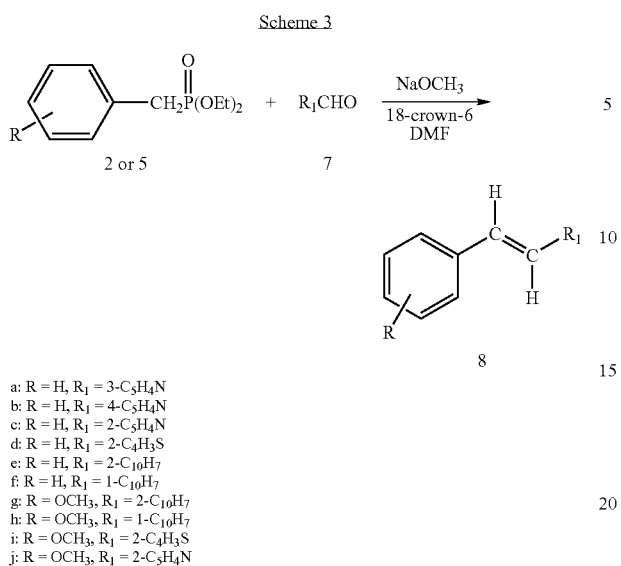

a: R = H, R₁ = 3-C₅H₄N
b: R = H, R₁ = 4-C₅H₄N
c: R = H, R₁ = 2-C₅H₄N
d: R = H, R₁ = 2-C₄H₃S
e: R = H, R₁ = 2-C₁₀H₇
f: R = H, R₁ = 1-C₁₀H₇
g: R = OCH₃, R₁ = 2-C₁₀H₇
h: R = OCH₃, R₁ = 1-C₁₀H₇
i: R = OCH₃, R₁ = 2-C₄H₃S
j: R = OCH₃, R₁ = 2-C₅H₄N

Cis-Stilbenes

The strategy used toward the synthesis of Z-stilbenes makes use of the classic Wittig olefination chemistry as described by Bellucci et al[1]. The methodology possesses the key advantage of stereoselectivity using the appropriate conditions. The ratio of the Z:E isomer was found to increase with decreasing temperature and the nature of the counterion of the phosphonium salt. Benzyltriphenylphosphonium iodides reacted with benzldehydes bearing both electron withdrawing and electron donating substituents to produce practically pure Z isomers. Reaction of the appropriately substituted phosphonium iodide salt (1) with substituted benzaldehydes (2) in dichloromethane using potassium hydroxide as the base in the presence of 18-crown-6 at −70° C. afforded substituted stilbenes (3) almost exclusively in the (Z)-conformation. Since the $R_1$ substituent on the phosphonium iodide salt and the $R_2$ substituent on the benzaldehyde can be many different groups, the number of different products (3) that can be formed is enormous.

Scheme 4

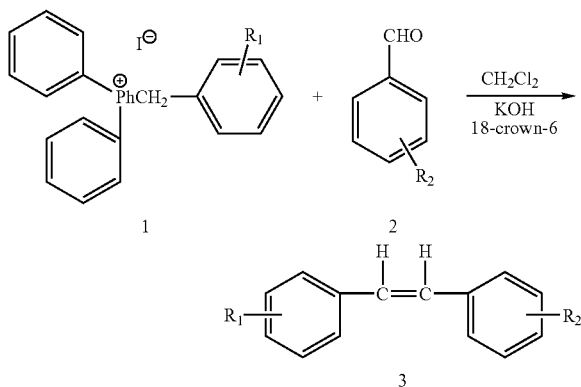

Figure 13:
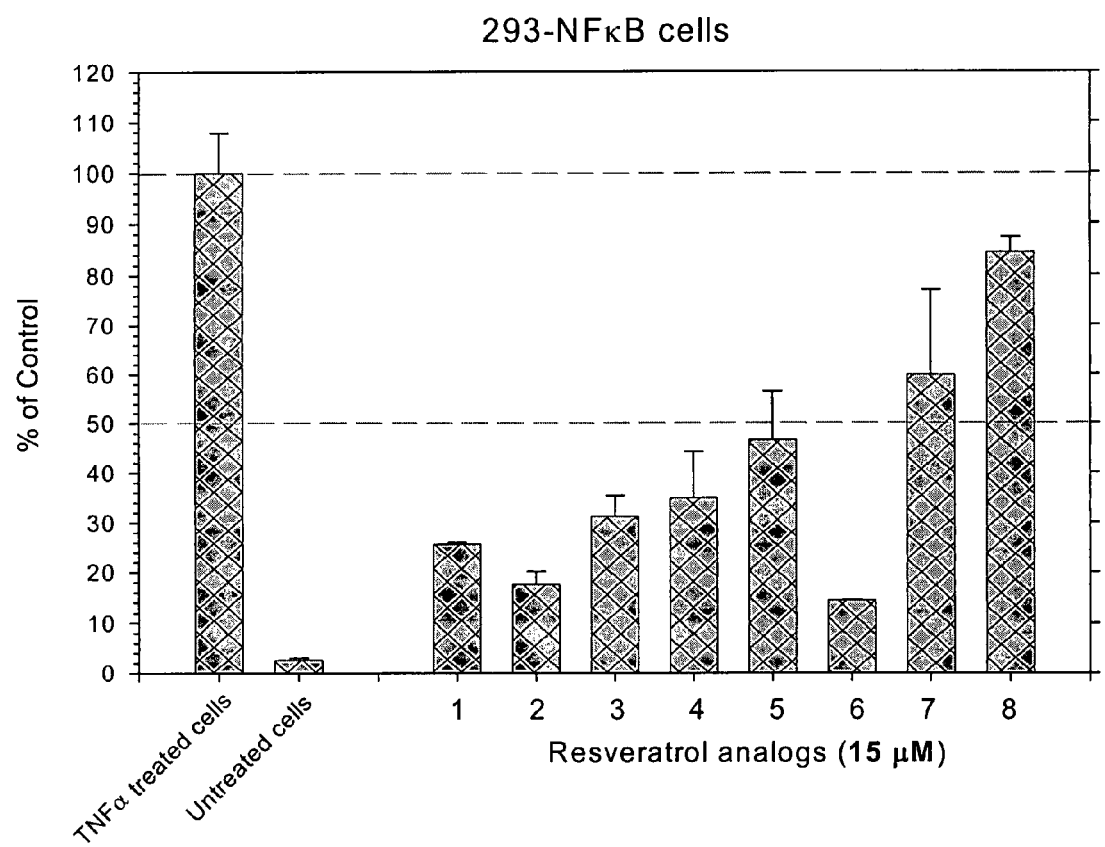
FIG. 13 shows the inhibition of the TNFα-induced activation of NF-κB by certain substituted cis-stilbenes (Scheme 4 and example).
Figure 13:
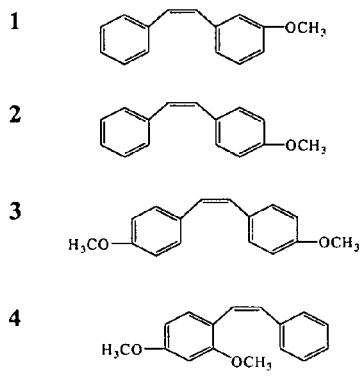
Figure 13:
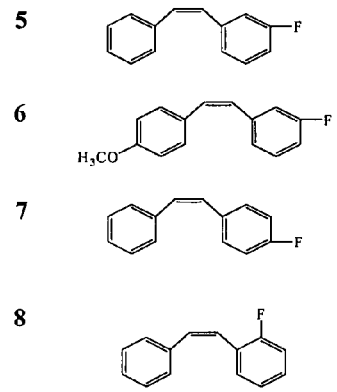

Using the above-synthetic method by analogy, a wide variety of cis-stilbenes may be synthesized by analogy with the synthesis of the trans-stilbenes, described above. These compounds were tested and the results are presented in FIG. 13.

Results

The first group of resveratrol analogs (FIG. 1) retain hydroxy functional groups on one or both of the aromatic rings. Resveratrol and 7 analogs were screened at 15 µM concentration. All of the analogs in this series retained anti-oxidant activity in the TRAP or FRAP assay. The total radical-trapping anti-oxidant parameter assay (TRAP assay) measures the ability of an analog to react with the pre-formed radical monocation of 2,2'-azinobis-(3-ethylbenzothiazoline-6-sulfonic acid) (ABTS-+). The ferric reducing/anti-oxidant power assay (FRAP assay) measures the ability of an analog to reduce a ferric tripyridyltriazine complex. Analogs 6cc and 6x were selected for further study. Analogs that also contained a methoxy functional group were the most active analogs in this series. Therefore, a separate series of substituted trans-stilbenes was synthesized that contained only methoxy groups.

Figure 2:
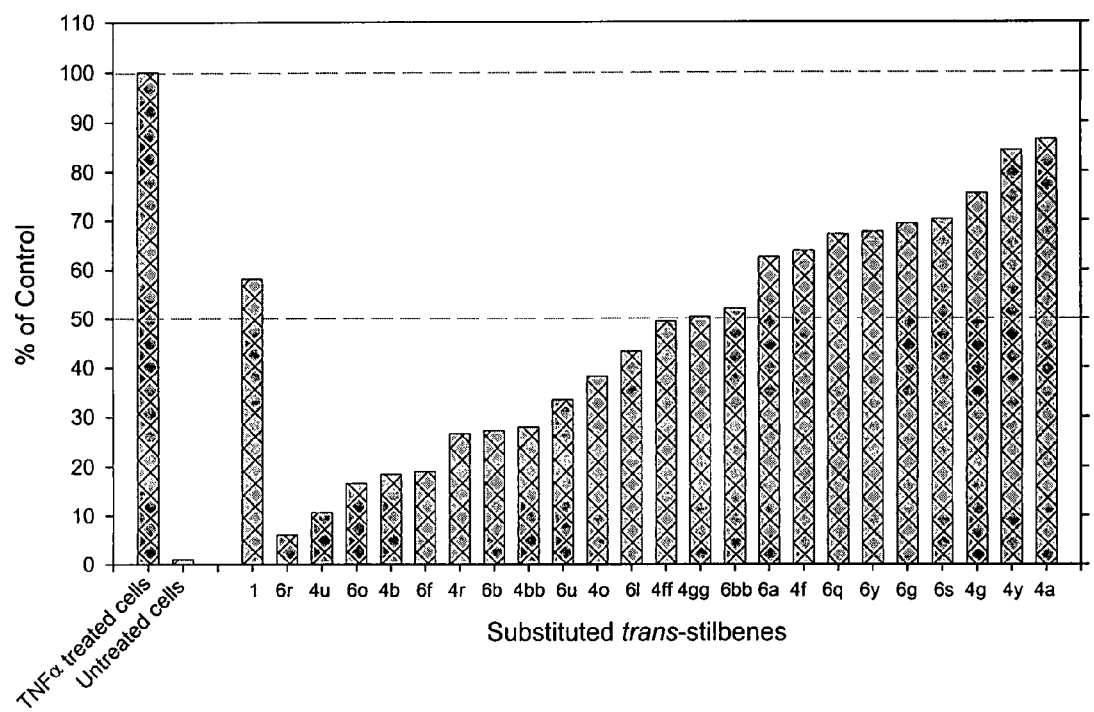
FIG. 2 shows the inhibition of the TNFα-induced activation of NF-κB by substituted trans-stilbenes containing only methoxy substituents (Schemes 1 and 2).

Twenty three stilbenes in the methoxy substituted series were screened and compared to resveratrol (FIG. 2). Fourteen of the 23 are more active than resveratrol as inhibitors of TNFα-induced activation of NFκB. Stilbene 6r was selected for additional study. None of the stilbenes in FIG. 2 retained anti-oxidant activity. Clearly, anti-oxidant activity is not essential for the ability of these compounds to prevent the TNFα-induced activation of NF-κB.

Figure 3:
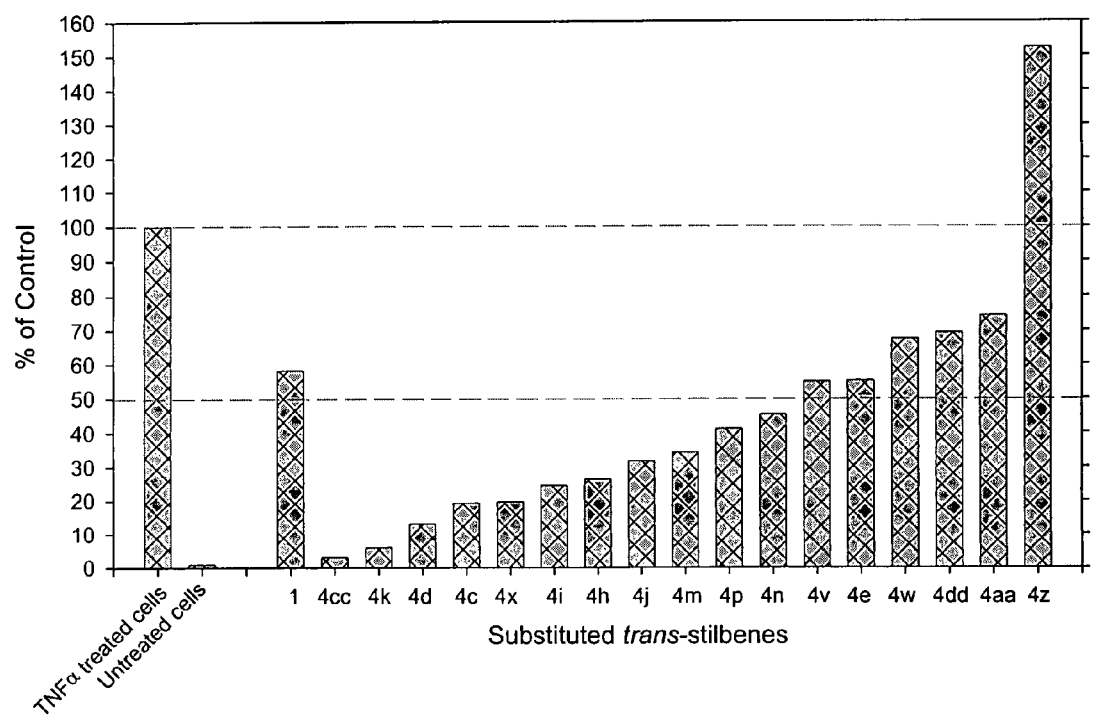
FIG. 3 shows the inhibition of the TNFα-induced activation of NF-κB by substituted trans-stilbenes devoid of phenolic or methoxy groups.

Seventeen substituted trans-stilbenes were synthesized that contained a variety of substituents other than hydroxy or methoxy groups on one of the rings and no substituent on the other ring. Thirteen of these were more active than resveratrol as inhibitors of TNFα-induced activation of NFκB in the preliminary screen (FIG. 3). Stilbenes 4cc and 4k were selected for further study. Only 4cc retained anti-oxidant activity.

Figure 4:
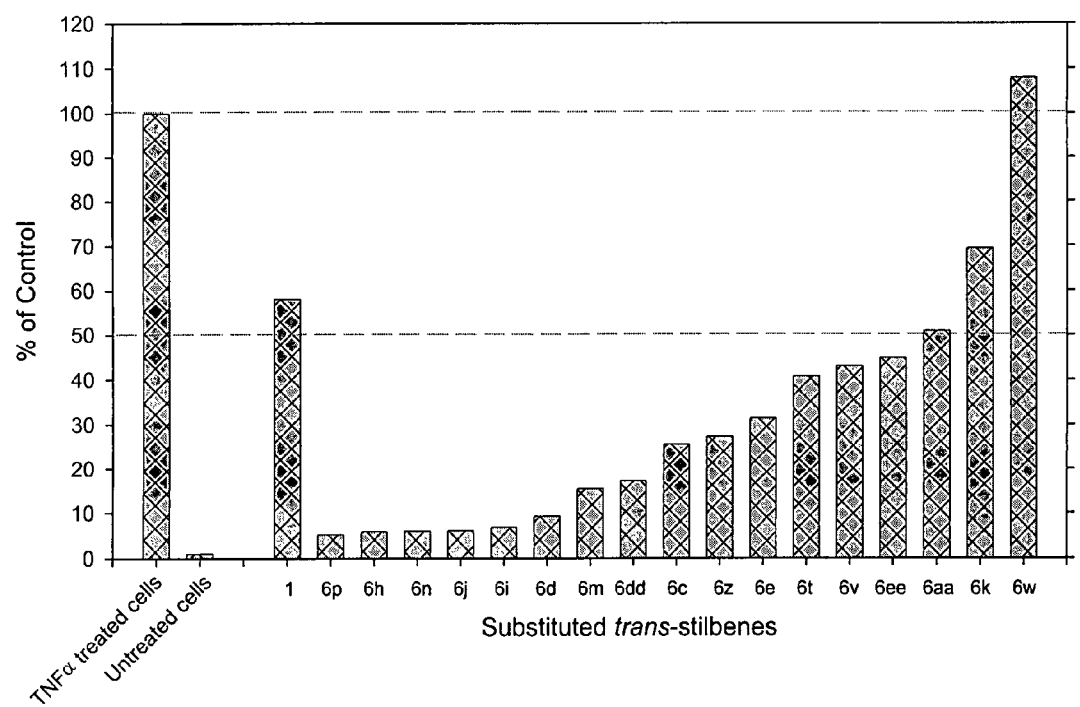
FIG. 4 shows the inhibition of the TNFα-induced activation of NF-κB by a series of trans-stilbenes devoid of phenolic groups (Scheme 2).

Seventeen substituted trans-stilbenes were synthesized that contained a variety of functional groups on one ring, excluding hydroxy groups, and having a methoxy group on the other ring (FIG. 4). Fifteen of these compounds are more active than resveratrol. Stilbenes 6p, 6h, 6n, 6j, 6i and 6d were selected for further study.

Figure 5:
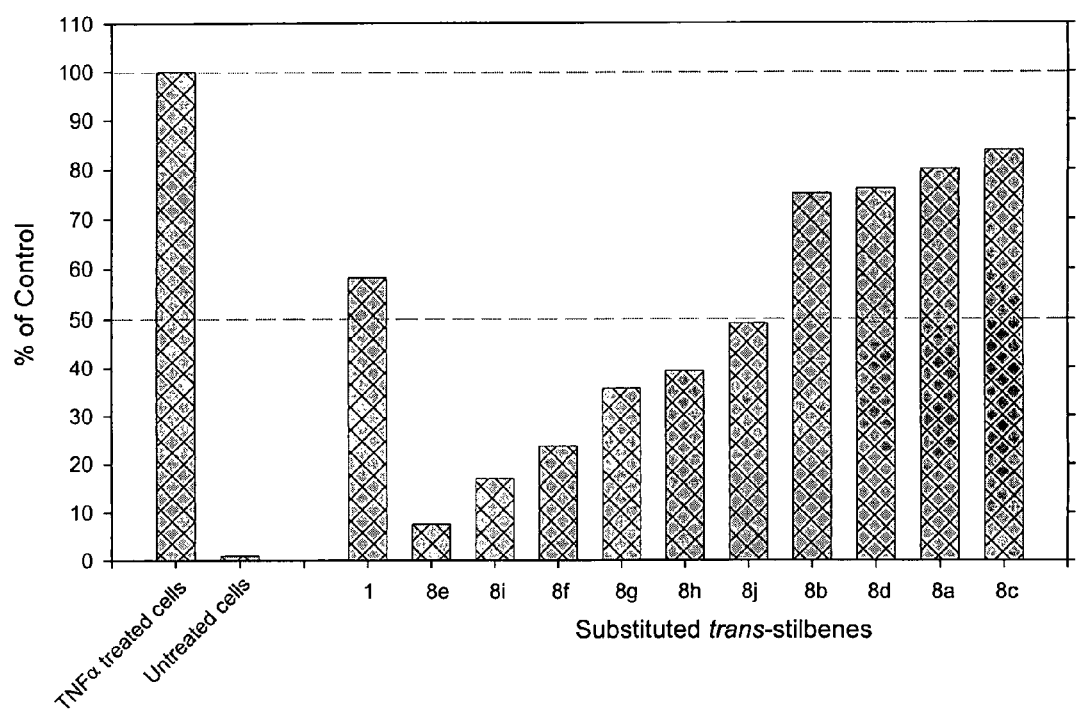
FIG. 5 shows the inhibition of the TNFα-induced activation of NF-κB by analogs of trans-stilbenes (Scheme 3).

Ten compounds were synthesized that contain one ring that is either a heterocyclic ring or a naphthalene ring (FIG. 5). These compounds are only remotely related to resveratrol. Four of these compounds have a methoxy group on one ring, and a number of these compounds are more active than resveratrol. Stilbene 8e was selected for further study.

Resveratrol and the 12 substituted trans-stilbenes that were selected for determination of $IC_{50}$ values were analyzed in triplicate. $IC_{50}$ values along with anti-oxidant activity and calculated ClogP values are summarized in Table 1. Several points are noteworthy. Some of the trans-stilbenes, such as compounds 4cc and 6p, are more than 100-fold more potent than resveratrol. Modest changes in the nature of the ring substituent or its location can markedly affect activity. Most of the compounds in Table 1 do not retain anti-oxidant activity. The toxicities of the 75 compounds evaluated in this study were determined. The initial screening that was carried out at 15 µM concentrations of resveratrol or substituted trans-stilbenes involved exposure of the cells to TNFα and to inhibitor for 7 hours. There was no apparent change in cell morphology. As a follow-up, the compounds in Table 1 were analyzed further by determination of cell viability, again after 7 hours and with exposure to 15 µM concentrations. In all cases, there was no loss in cell viability compared to untreated controls.

TABLE 1

IC$_{50}$ values of resveratrol and substituted trans-stilbenes
for inhibition of the TNFα-induced activation of NFκB.

| Number | Structure | IC$_{50}$(μM) | Anti-oxidant Activity | | CLogP |
| --- | --- | --- | --- | --- | --- |
| | | | TRAP | FRAP | |
| 1 resveratrol | 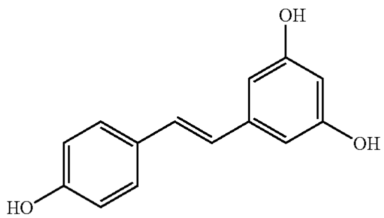 [SMILES: Oc1ccc(/C=C/c2cc(O)cc(O)c2)cc1] | 20 ± 3 | + | + | 2.833 |
| 6cc | 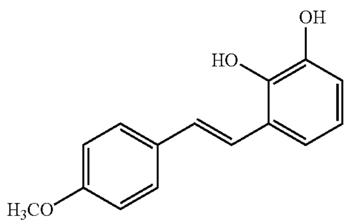 [SMILES: COc1ccc(/C=C/c2cccc(O)c2O)cc1] | 0.5 ± 0.3 | + | + | 3.089 |
| 6x | 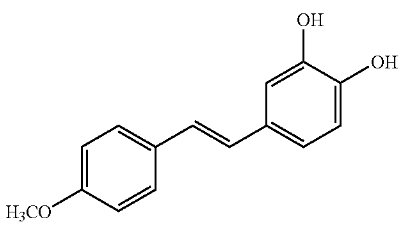 [SMILES: COc1ccc(/C=C/c2ccc(O)c(O)c2)cc1] | 0.6 ± 0.4 | + | + | 3.089 |
| 6r | 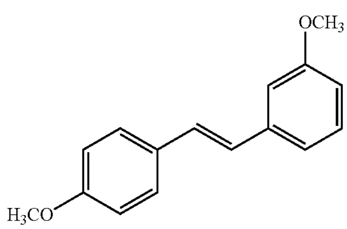 [SMILES: COc1ccc(/C=C/c2cccc(OC)c2)cc1] | 0.6 ± 0.1 | − | − | 4.272 |
| 4cc | 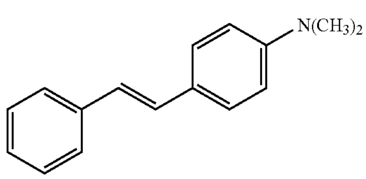 [SMILES: CN(C)c1ccc(/C=C/c2ccccc2)cc1] | 0.15 ± 0.1 | + | + | 4.599 |
| 4k | 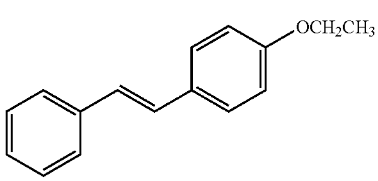 [SMILES: CCOc1ccc(/C=C/c2ccccc2)cc1] | 0.3 ± 0.03 | − | − | 4.882 |
| 6p | 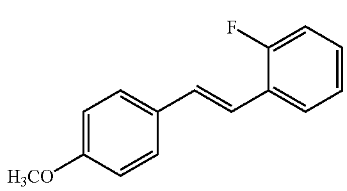 [SMILES: COc1ccc(/C=C/c2ccccc2Cl)cc1] | 0.15 ± 0.1 | − | − | 4.496 |

TABLE 1-continued

IC$_{50}$ values of resveratrol and substituted trans-stilbenes
for inhibition of the TNFα-induced activation of NFκB.

| Number | Structure | IC$_{50}$(μM) | Anti-oxidant Activity | | CLogP |
| --- | --- | --- | --- | --- | --- |
| | | | TRAP | FRAP | |
| 6h | 4-MeO-C6H4-CH=CH-C6H4-3-Cl | 1.0 ± 0.1 | – | – | 5.066 |
| 6n | 4-MeO-C6H4-CH=CH-C6H4-3-F | 1.1 ± 0.6 | – | – | 4.496 |
| 6j | 4-MeO-C6H4-CH=CH-C6H4-2-Cl | 1.5 ± 0.03 | – | – | 5.066 |
| 6i | 4-MeO-C6H4-CH=CH-C6H4-3-CH3 | 0.8 ± 0.2 | – | – | 4.852 |
| 6d | 4-MeO-C6H4-CH=CH-C6H4-4-CH3 | 0.9 ± 0.1 | – | – | 4.852 |
| 8e | C6H5-CH=CH-(2-naphthyl) | 1.3 ± 0.3 | – | – | 5.608 |

Figure 6:
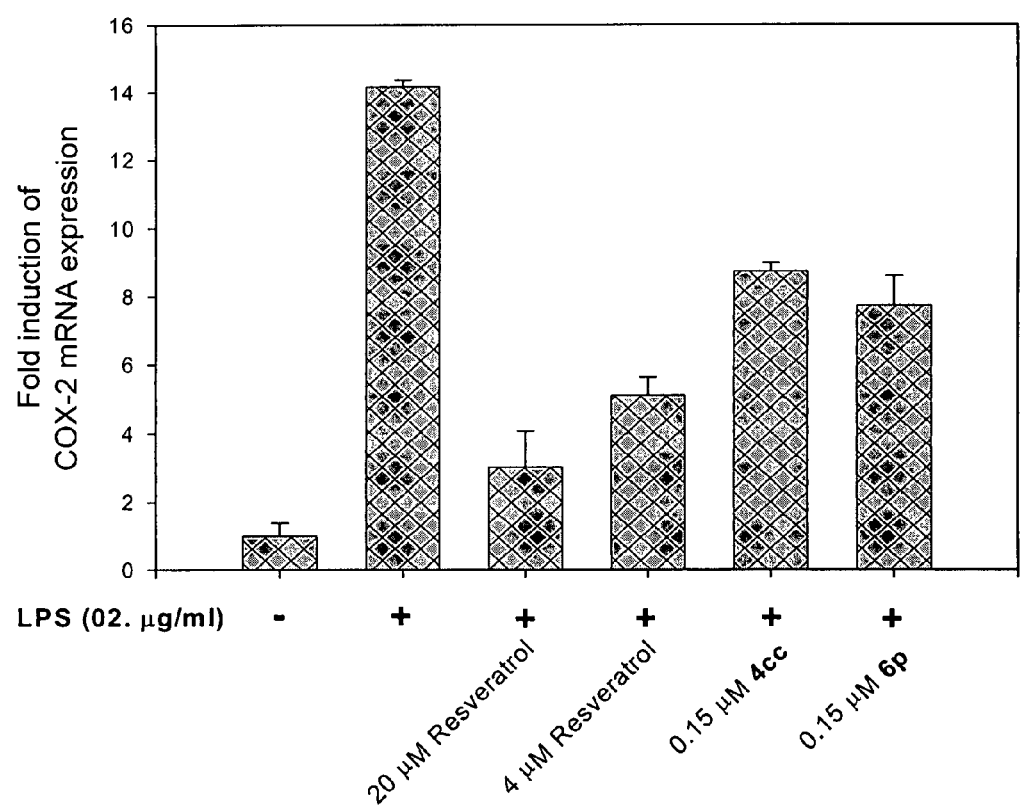
FIG. 6 shows the inhibitory effects of resveratrol and analogs 4cc and 6p on LPS-induced expression of COX-2 mRNA in BV-2 microglial cells. Error bars represent standard deviations, n=3.
Figure 7:
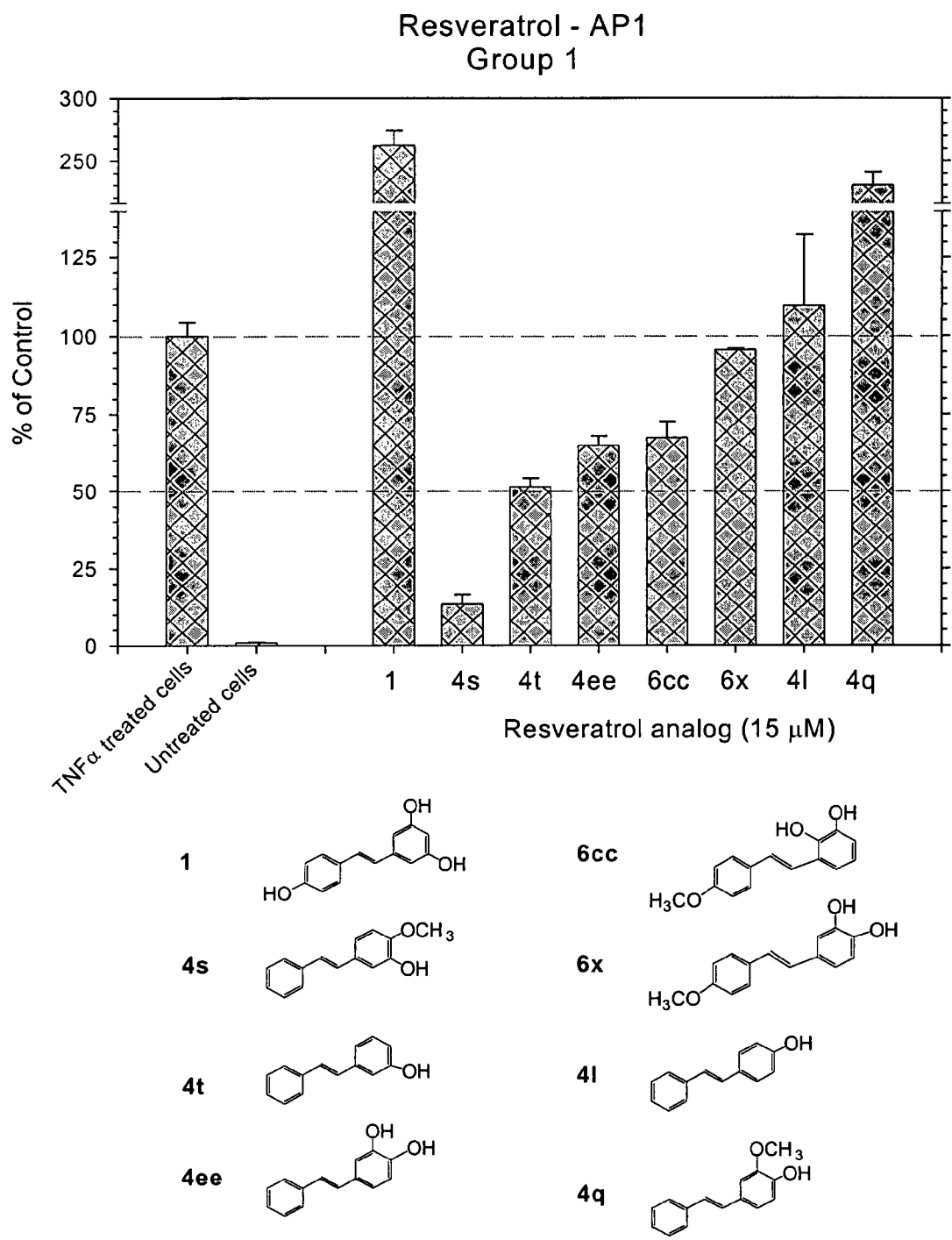
FIGS. 7-12 show the effects of compounds according to the present invention in AP-1 assays as otherwise described hereing.
Figure 8:
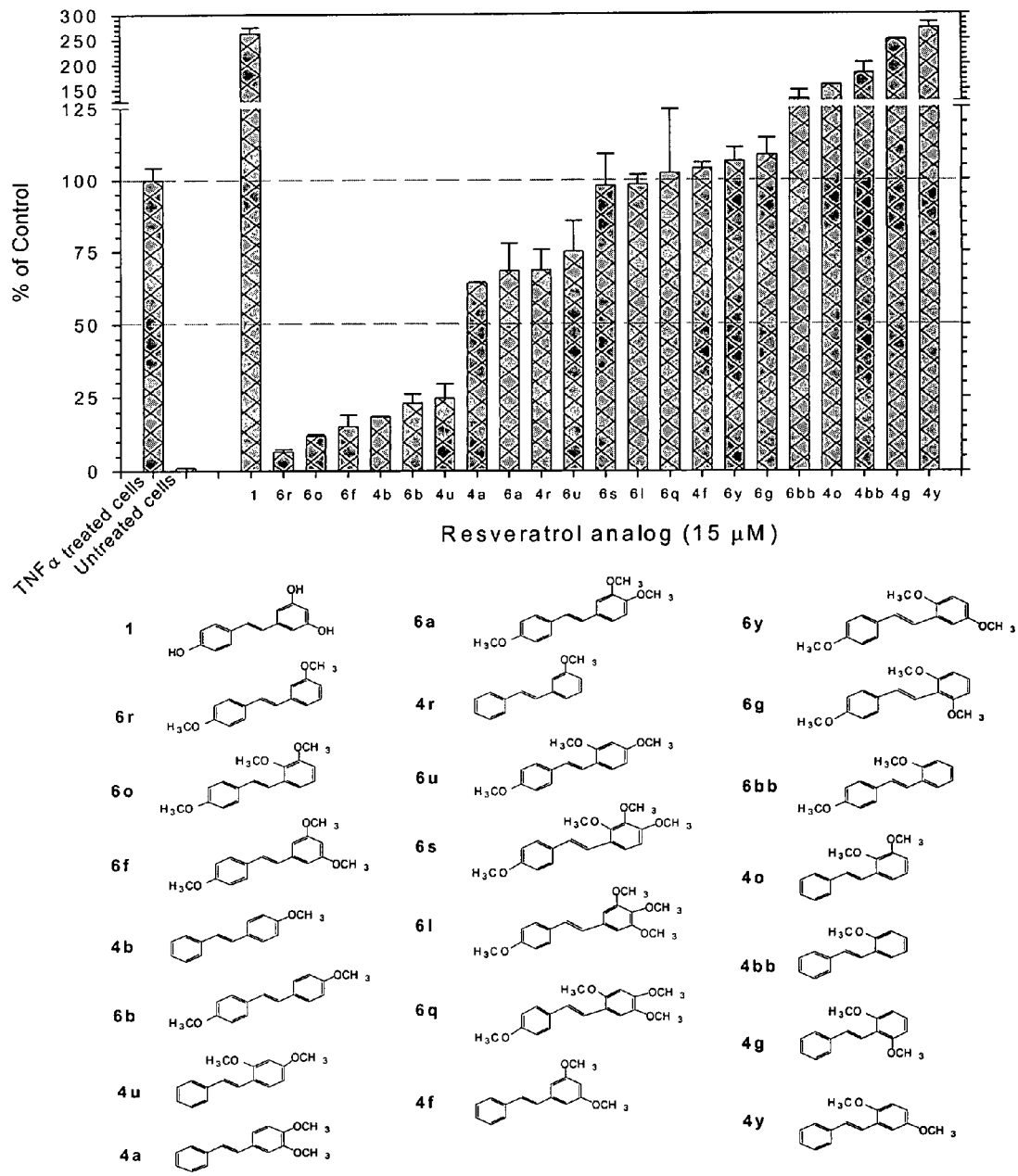
Figure 9:
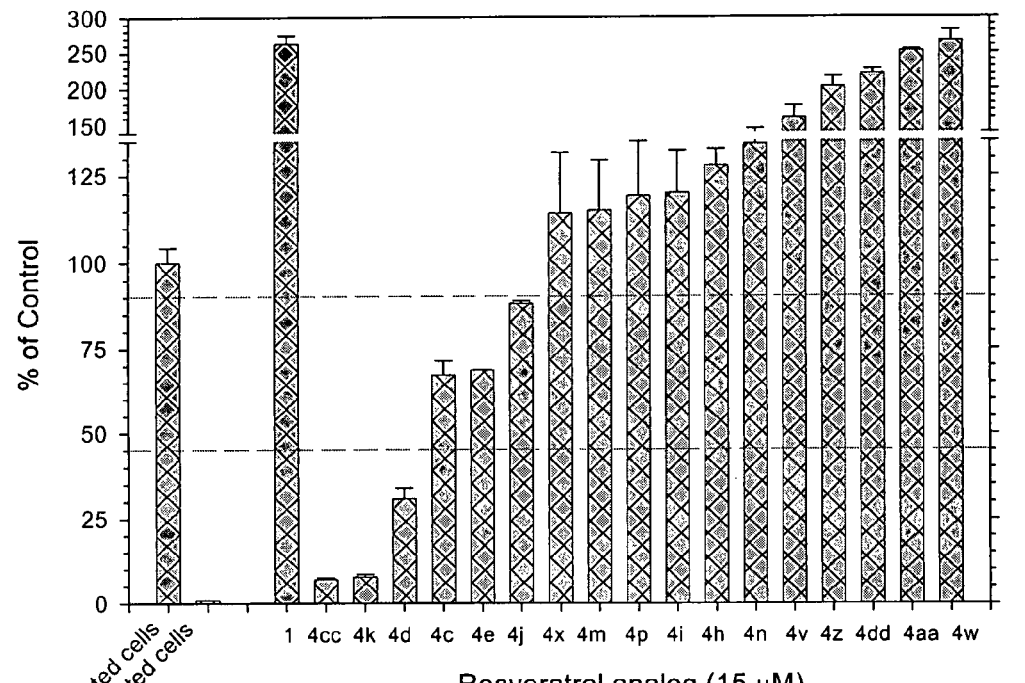
Figure 9:
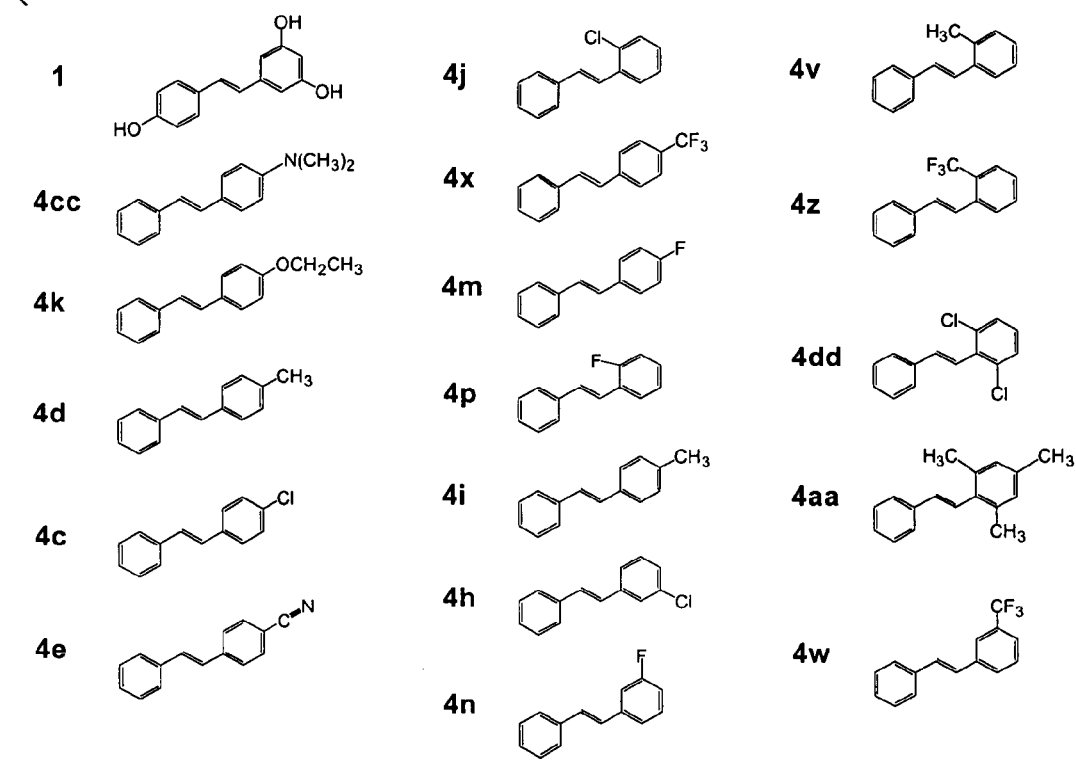
Figure 10:
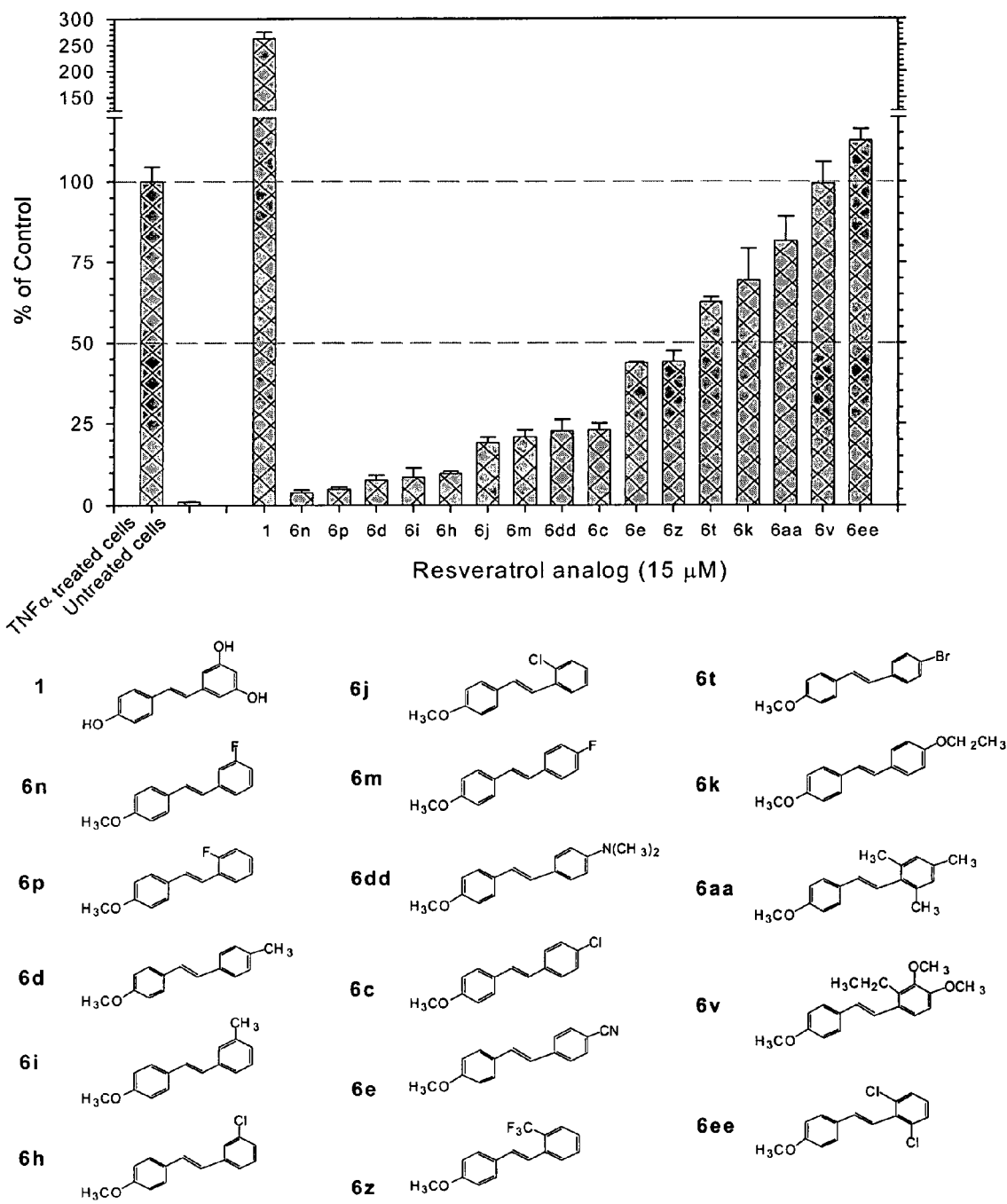
Figure 11:
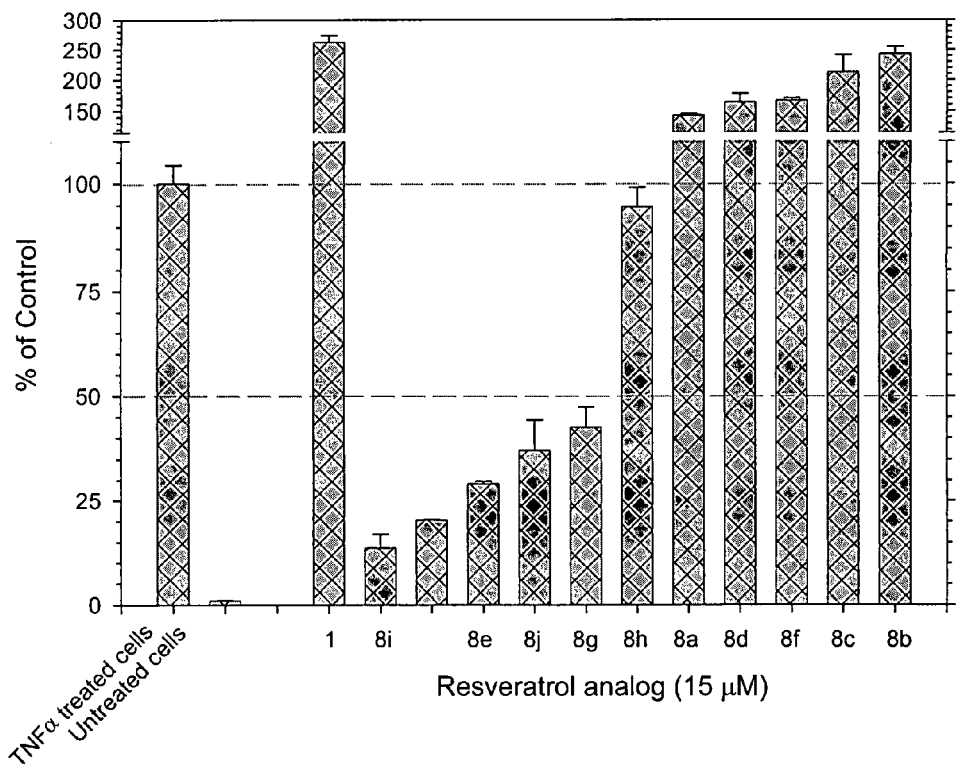
Figure 11:
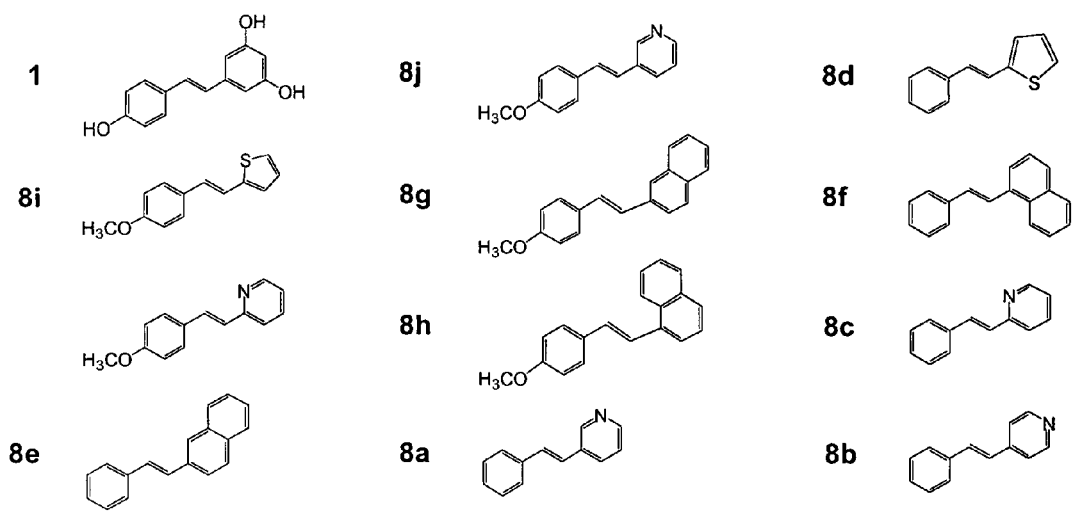
Figure 12:
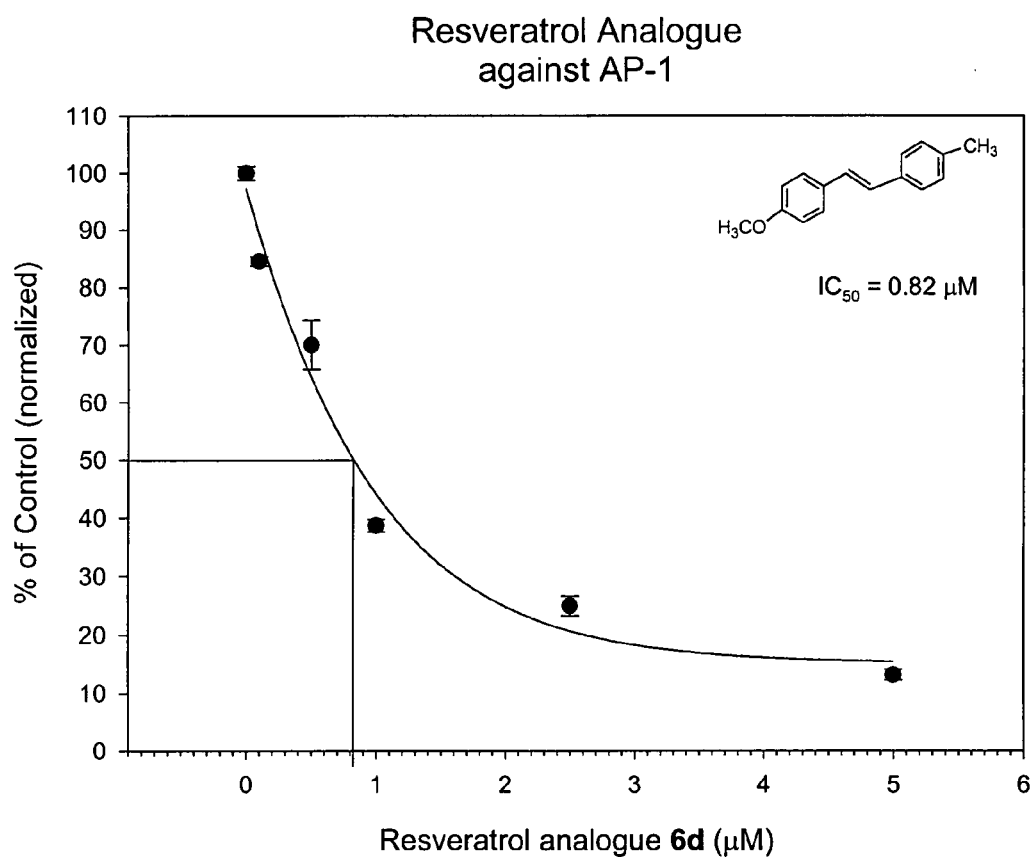

To determine whether the effects of resveratrol and its analogs in inhibiting the activation of NF-κB extend beyond the cell line used for screening, resveratrol and analogs 4cc and 6p were compared using microglial BV-2 cells. This cell line has been shown to express COX-2 in response to LPS stimulation by an NF-κB-dependent pathway.[33] BV-2 cells stimulated with LPS showed a strong induction of COX-2 mRNA (FIG. 6) that was markedly suppressed by 20 μM resveratrol and about 50% inhibited by 4 μM resveratrol. Analog 4cc and analog 6p at 0.15 μM concentrations were almost as effective as 4 μM resveratrol, consistent with the conclusions from Table 1 that these two analogs are more potent than resveratrol.

Resveratrol is one of several polyhydroxylated stilbene natural products with biological activity. Piceatannol (9) (figure below), which is present in the seeds of *Euphorbia lagascae*, is similar to resveratrol except for the presence of an additional hydroxyl functional group. Piceatannol exhibits anti-inflammatory and anti-proliferative activities[17] and induces apoptosis in lymphoma cells.[34] Piceatannol, like resveratrol, also inhibits TNF-induced activation of NF-κB whereas stilbene itself is inactive.[35] Pterostilbene (10) and 3'-hydroxypterostilbene (11) (figure below) are natural analogs of resveratrol and piceatannol, respectively, that exhibit chemopreventive and apoptosis-inducing activities.[36,37] These two analogs as well as resveratrol itself show markedly different apoptosis-inducing activities against sensitive and resistant leukemia cells,[37] suggesting that minor structural changes in these hydroxylated stilbenes have major effects on biological activity.[21] However, all of these natural products retain one or more phenolic groups, which have been generally assumed to contribute both to anti-oxidant and to biological activities.

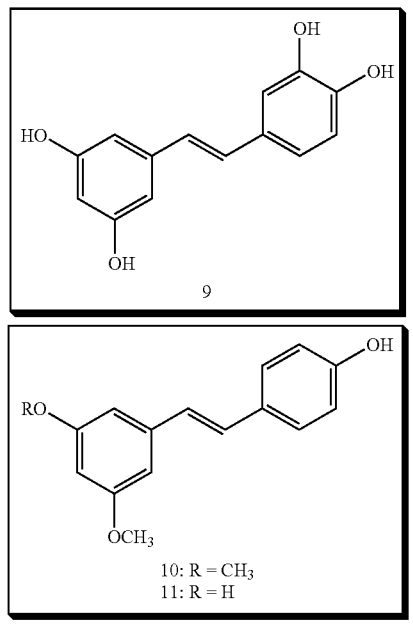

10: R = CH₃
11: R = H

The trans-stilbenes in FIG. 1 are analogs of resveratrol and related natural products. All of these analogs of resveratrol contain one or more hydroxy groups, and some of these analogs also contain methoxy groups. It is not surprising that this group of resveratrol analogs retains activity, in view of the reported activities for resveratrol, piceatannol and related compounds.[21,35-37] The activities of the analogs in FIG. 1 as inhibitors of the TNFα-induced activation of NF-κB, however, vary considerably; some compounds, such as analogs 6cc, 4s and 6x, are considerably more active than resveratrol. These three analogs contain one or two hydroxy groups and a single methoxy group. Therefore, it was of interest to evaluate trans-stilbenes that were devoid of hydroxy groups and would not be expected to exhibit anti-oxidant activity and to determine whether these compounds were still effective as inhibitors of the activation of NF-κB.

The 23 trans-stilbenes in FIG. 2 contain one or more methoxy groups and include compounds with methoxy groups on both of the aromatic rings. None of these methoxy-substituted trans-stilbenes retained anti-oxidant activity in either the TRAP assay or the FRAP assay. Nevertheless, many of these compounds are more active than resveratrol as inhibitors of the TNFα-induced activation of NF-κB. This includes trans-stilbenes 6r, 4u, 6o, 4b and 6f that are especially active and contain one to three methoxy groups, either on one or on both rings and in different positions. Other compounds in this group, such as 6b and 4o, are isomers of 6r but retained very little activity whereas 6r is highly active.

Some of the most active trans-stilbenes contain substituents other than hydroxy or methoxy groups (FIGS. 3 and 4) and include compounds with substituents on one or both rings. trans-Stilbene 4cc with a dimethylamino substituent in the 4-position and trans-stilbene 6p with 2-fluoro- and 4'-methoxy substituents were the most active of the 75 compounds included in this study; both 4cc and 6p showed IC₅₀ values of 0.15 μM, which is >100-fold more potent than resveratrol. Compound 4cc exhibits anti-oxidant activity in both the FRAP and TRAP assays, whereas compound 6p does not exhibit anti-oxidant activity.

The actual target(s) whereby the most active substituted trans-stilbenes (Table 1) inhibit the TNFα-induced activation of NF-κB remains to be identified. Resveratrol has been shown to suppress the TNF-induced phosphorylation and nuclear translocation of the p65 subunit of NF-κB.[38] Both IKKα and IKKβ are able to catalyze the phosphorylation of p65, although through different signaling pathways,[39] and are potential targets. Likewise, one or more of the kinases that activate IKK by phosphorylation, in response to TNFα or to the numerous other activators of NF-κB,[35] may be the targets.

Conclusions

We have demonstrated that the activation of NF-κB by TNFα can be effectively inhibited by a wide range of substituted trans-stilbenes, many of which do not contain hydroxyl functional groups and, therefore, are no longer analogs of resveratrol and related natural products. Compounds were identified that were devoid of anti-oxidant activity but were at least 100-fold more potent than resveratrol.

The present invention is illustrated by the following examples/experimental. It is to be understood that the particular examples, materials, amounts, and procedures are to be interpreted broadly in accordance with the scope and spirit of the invention as set forth herein.

Experimental Section

Assay of the Anti-oxidant Activities of Resveratrol and Substituted Trans-stilbenes The anti-oxidant activities of resveratrol and substituted trans-stilbenes were determined using two standard assays,[40] the TRAP assay[41] and the FRAP assay.[42] For the TRAP assay, 2,2'-azinobis-(3-ethylbenzothiazoline-6-sulfonic acid) (ABTS) was reacted with potassium persulfate in the dark, overnight, to generate the colored ABTS⁺ radical cation, which has an absorption maximum at 734 nm. The activities of resveratrol and the series of substituted trans-stilbenes were determined by their abilities to quench the color of the radical cation. For the FRAP assay, the ferric complex of 2,4,6-tripyridyl-s-triazine was prepared at acidic pH, and the anti-oxidant activities of resveratrol and the substituted trans-stilbenes were determined by their abilities to reduce the ferric complex to the ferrous complex, monitored by formation of the ferrous complex at 593 nm. In both colorimetric assays, the vitamin E analog Trolox was used as a control.

Cell Assay

An NF-κB reporter stable cell line derived from human 293T embryonic kidney cells (293T/NF-κB-luc) (Panomics, Inc., Redwood City, Calif.) was grown in a humidified atmosphere at 37° C. in 5% CO₂/95% air. The cells were maintained in Dulbecco's Modified Eagle's Medium (DMEM—high glucose containing 4 mM glutamine) supplemented with 10% fetal bovine serum (FBS), 1 mM sodium pyruvate, 100 units/ml penicillin, 100 µg/ml streptomycin and 100 µg/ml hygromycin (Gibco/Invitrogen, Carlsbad, Calif.) to maintain cell selection. One day prior to treatment, the 293T/NFκB-luc cells were plated into 24-well cell culture plates (Costar, Cambridge, Ma.) at approximately 70% confluency in the above media without hygromycin. The following day cells were fed fresh media 1 hour prior to treatment. Media with or without recombinant tumor necrosis factor alpha (TNFα) (R&D Biosciences/Clontech, Palo Alto, Calif.) was then applied to the cells at 20 ng/ml followed by immediate treatments with resveratrol or substituted trans-stilbene. The cells were placed again in a humidified atmosphere at 37° C. in 5% $CO_2$/95% air for 7 hours. Plate wells were gently washed with phosphate buffered saline, pH 7.4, and lysed with 1x passive lysis buffer (Promega, Madison, Wis.). The subsequent lysates were analyzed with the Luciferase Assay System (Promega) utilizing a TD-20/20 luminometer (Turner Designs, Sunnyvale, Calif.). The firefly luciferase relative light units were normalized to protein (mg/ml) with BCA™ Protein Assay Kit (Pierce, Rockford, Ill.) and standardized to percent of control (TNFα control).

For assays of cell viability, cells were treated similarly as above and with 15 µM substituted trans-stilbene. After washing, cells were treated with 100 µl media and 20 µl CellTiter 96® $AQ_{ueous}$ One Solution reagent for 1 hour and then read at 490 nm with a Spectromax plate reader.

Inhibition of COX-2 Expression by Resveratrol and Analogs

Mouse microglial cells (BV-2) were cultured in RPMI-1640 (Cellgro, Herndon, Va.) supplemented with 10% FBS, 1 mM sodiumn pyruvate, 2 mM L-glutamine, 100 µg/ml streptomycin sulfate and 100 units/ml penicillin. Cells were grown on culture plates, pre-treated with 1% gelatin for 30 min, at 37° C. and passaged twice weekly. BV-2 cells were activated with 0.2 µg/ml lipopolysaccharide (LPS) (Sigma, St. Louis, Mo.). Those cells that were treated with LPS were incubated in parallel with resveratrol or resveratrol analogs 4cc or 6p for 24 hours at the indicated concentrations. Total RNA was purified using RNeasy (Qiagen, Valencia, Calif.) and converted to cDNA using TaqMan Reverse Transcriptase (Applied Biosystems, Branchburg, N.J.). Cyclooxygenase-2 (COX-2) mRNA levels were measured using quantitative Real Time PCR analysis (qRT-PCR) of cDNA samples. Primers specific for COX-2 were designed to amplify a 132 base pair sequence flanking intron 7. Primer sequences for COX-2 were: upstream, TGGGGTGATGAGCAACTATT; downstream, AAGGAGCTCTGGGTCAAACT. qRT-PCR was performed using ABsolute QPCR SYBR Green Mix (Fisher Scientific, Atlanta, Ga.) with the following cycling parameters: 1 cycle, 95° C., 15 min; 40 cycles, 95° C., 15 sec, 60° C., 1 min. β-Actin mRNA levels were quantitated using identical cycling conditions and used to normalize values obtained for COX-2 expression.

TPA-induced Up-regulation of Activator Protein-1-Effects of Stilbenes

Assay of the Anti-oxidant Activities of Stilbene Analogs

The anti-oxidant activities of certain stilbene analogs according to the present invention were determined using two standard assays. See, Schlesier, et al., Free Rad Res. 2002; 36:177-187. The total radical-trapping anti-oxidant parameter assay (TRAP assay) measures the ability of an analog to react with the pre-formed radical monocation of 2,2'-azino-bis-(3-ethylbenzothiazoline-6-sulfonic acid) (ABTS$^+$). See, Re, et al., *Free Rad Biol Med,* 26:1231-1237 (1999). ABTS was reacted with potassium persulfate in the dark, overnight, to generate the colored ABTS$^+$ radical cation, which has an absorption maximum at 734 nm. The activities of curcumin and analogs were determined by their abilities to quench the color of the radical cation. The ferric reducing/anti-oxidant power assay (FRAP assay) measures the ability of an analog to reduce a ferric tripyridyltriazine complex. See, Benzie and Strain, *Meth Enzymol,* 299:15-27 (1999). The ferric complex of 2,4,6-tripyridyl-s-triazine was prepared at acidic pH, and the anti-oxidant activities of curcumin and analogs were determined by their abilities to reduce the ferric complex to the ferrous complex, monitored by formation of the ferrous complex at 593 nm. In both colorimetric assays, the vitamin E analog Trolox was used as a control.

Assay of the Activities of Stilbene Analogs as Inhibitors of the TPA-induced Activation of AP-1

An AP-1 reporter stable cell line derived from human 293T embryonic kidney cells transfected with a luciferase reporter construct containing three AP-1 binding sites in the promoter (293T/AP-1-luc, Panomics, Inc., Redwood City, Calif.) was grown in a humidified atmosphere at 37° C. in 5% $CO_2$/95% air. The cells were maintained in Dulbecco's Modified Eagle's Medium (DMEM—high glucose containing 4 mM glutamine) supplemented with 10% fetal bovine serum (FBS), 1 mM sodium pyruvate, 100 units/ml penicillin, 100 µg/ml streptomycin and 100 µg/ml hygromycin (Gibco/Invitrogen, Carlsbad, Calif.) to maintain cell selection. One day prior to treatment, the 293T/AP-1-luc cells were plated into 24-well cell culture plates (Costar, Cambridge, Ma.) in the above media without hygromycin. The following day, the cells, which were at approximately 60% confluency, were fed fresh media with or without TPA, 10 ng/ml, (Calbiochem) and immediately treated with curcumin or analog prepared in DMSO stock solutions. The cells were placed again in a humidified atmosphere at 37° C. in 5% $CO_2$/95% air for 24 hours. Plate wells were gently washed with phosphate buffered saline, pH 7.4, and lysed with 1x passive lysis buffer (Promega, Madison, Wis.). The subsequent lysates were analyzed with the Luciferase Assay System (Promega) utilizing a TD-20/20 luminometer (Turner Designs, Sunnyvale, Calif.). The firefly luciferase relative light units were normalized to protein (mg/ml) with BCA™ Protein Assay Kit (Pierce, Rockford, Ill.) and standardized to percent of control (TPA control).

The results for a number of the stilbene compounds according to the present invention which were assayed as described above are set forth in the following Table 2 as well as the attached FIGS. 7-12. As can be seen from the presented data, the stilbene compounds according to the present invention exhibit significant activity against AP-1.

TABLE 2

IC$_{50}$ values of resveratrol and substituted trans-stilbenes
for inhibition of the TPA-induced activation of AP-1.

| Number | Structure | IC$_{50}$(μM) | Anti-oxidant Activity | | CLogP |
| --- | --- | --- | --- | --- | --- |
| | | | TRAP | FRAP | |
| Resveratrol 1 | 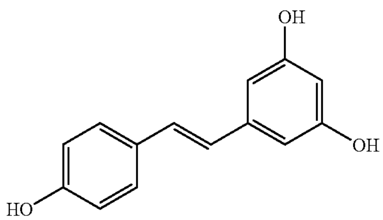 [SMILES: Oc1ccc(/C=C/c2cc(O)cc(O)c2)cc1] | activated | + | + | 2.833 |
| 4b | 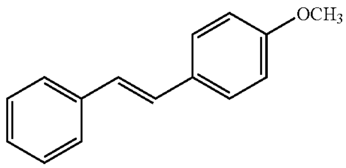 [SMILES: COc1ccc(/C=C/c2ccccc2)cc1] | 1.3 ± 0.03 | − | + | 4.753 |
| 4d | 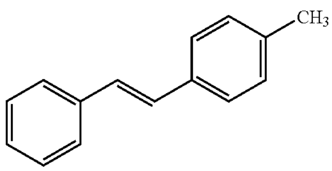 | 1.6 ± 0.6 | − | + | 5.333 |
| 4k | 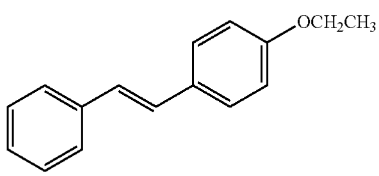 [SMILES: CCOc1ccc(/C=C/c2ccccc2)cc1] | 0.8 ± 0.1 | − | + | 5.282 |
| 4t | 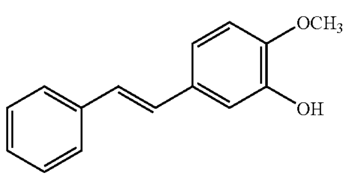 [SMILES: COc1ccc(/C=C/c2ccccc2)cc1O] | 0.8 ± 0.05 | + | + | 4.016 |
| 4cc | 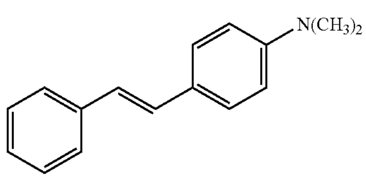 [SMILES: CN(C)c1ccc(/C=C/c2ccccc2)cc1] | 1.1 ± 0.1 | + | + | 4.999 |
| 6r | 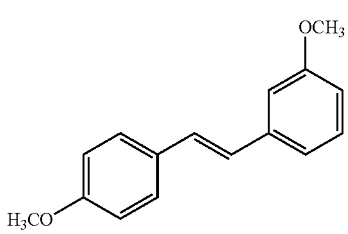 [SMILES: COc1ccc(/C=C/c2cccc(OC)c2)cc1] | 0.7 ± 0.04 | − | − | 4.672 |

TABLE 2-continued
IC$_{50}$ values of resveratrol and substituted trans-stilbenes for inhibition of the TPA-induced activation of AP-1.
| Number | Structure | IC$_{50}$(μM) | Anti-oxidant Activity | | CLogP |
|---|---|---|---|---|---|
| | | | TRAP | FRAP | |
| 6i | 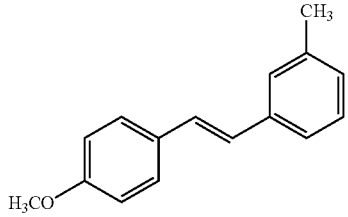 | 1.0 ± 0.12 | – | – | 5.252 |
| 6f | 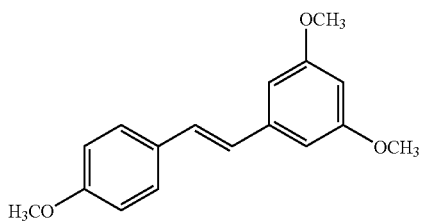 [SMILES: COc1ccc(/C=C/c2cc(OC)cc(OC)c2)cc1] | 3.8 ± 1.1 | – | – | 4.761 |
| 6o | 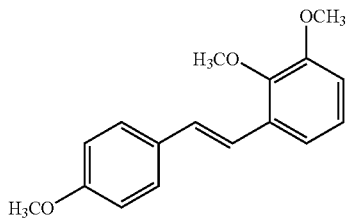 [SMILES: COc1ccc(/C=C/c2cccc(OC)c2OC)cc1] | 2.4 ± 0.7 | – | – | 4.411 |
| 8i | 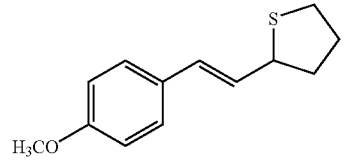 | 2.5 ± 0.5 | – | – | 4.399 |
| 6p | 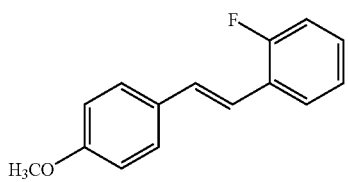 [SMILES: COc1ccc(/C=C/c2ccccc2F)cc1] | 0.8 ± 0.1 | – | – | 4.896 |
| 6n | 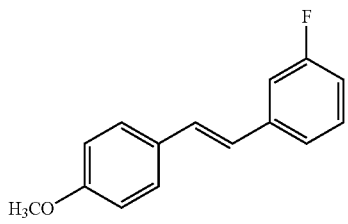 | 0.5 ± 0.1 | – | – | 4.896 |
| | 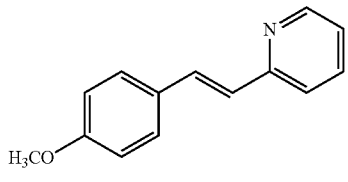 [SMILES: COc1ccc(/C=C/c2ccccn2)cc1] | 2.1 ± 0.4 | – | – | 3.256 |

TABLE 2-continued

IC$_{50}$ values of resveratrol and substituted trans-stilbenes
for inhibition of the TPA-induced activation of AP-1.

| Number | Structure | IC$_{50}$(μM) | Anti-oxidant Activity | | CLogP |
| --- | --- | --- | --- | --- | --- |
| | | | TRAP | FRAP | |
| 6h | H$_3$CO–C$_6$H$_4$–CH=CH–C$_6$H$_4$–Cl | 0.8 ± 0.15 | – | – | 5.466 |
| 6d | H$_3$CO–C$_6$H$_4$–CH=CH–C$_6$H$_4$–CH$_3$ | 0.8 ± 0.03 | – | – | 5.252 |

Chemical Synthesis

General Method for Synthesis of (E) Stilbenes

To a solution of phosphonic acid diethyl ester (5 mmol) in 10 mL of dry DMF there was added sodium methoxide (10 mmol) and 18/6 crown ether (2 mmol). The resulting mixture was stirred at room temperature for five minutes and the appropriate aldehyde or hydroxybenzaldehyde methoxymethyl ether (6 mmol) dissolved in 5 mL of DMF was added dropwise at 0° C. The mixture was stirred at room temperature for one hour and then for five hours at 120° C. The reaction was quenched by pouring into 200 mL of water with stirring. Reactions that gave solids were filtered and recrystallized from hexane or ethanol. Reactions that gave oils were extracted into ether and the ether layer was washed with water, saturated salt and dried (MgSO$_4$). Filtration and evaporation of the ether afforded oily solids that were purified by recrystallization or chromatography (hexane/ethyl acetate). Methoxymethyl protected hydroxystilbenes were heated in methanol containing 2 drops of concentrated hydrochloric acid to give hydroxystilbenes.[43]

(E)-2,6-Dimethoxystilbene (4g). mp 45-46° C.; $^1$H NMR: δ 3.89 (s, 6H), 7.18 (m, 6H), 7.33 (t, 1H, J=7.35 Hz), 7.45 (d, 1H, J=16.68 Hz), 7.53 (d, 2H, J=6.75 Hz). Exact mass calcd for C$_{16}$H$_{16}$O$_2$:240.1550, observed (M+H) 241.1228.

(E)-3-Hydroxy-4-methoxystilbene (4s). mp 149-153° C.; $^1$H NMR: δ 3.88 (s, 3H), 5.65 (s, 1H), 6.82 (d, 1H, J=8.34 Hz), 6.97 (m, 3H), 7.15 (s, 1H, J=1.98 Hz), 7.23 (m, 1H), 7.34 (t, 2H, J=7.35 Hz), 7.48 (d, 2H, J=7.15 Hz). Exact mass calcd for C$_{15}$H$_{14}$O$_2$:226.0994, observed (M+H) 227.1072.

(E)-2-Trifluoromethylstilbene (4z). oil; $^1$H NMR: δ 7.07 (d, 1H, J=16.09 Hz), 7.36 (m, 5H), 7.52 (m, 3H), 7.65 (d, 1H, J=7.75 Hz), 7.77 (d, 1H, J=7.95 Hz). Exact mass calcd for C$_{15}$H$_{11}$F$_3$:248.0813, observed (M+H) 249.0891.

(E)-2,6-Dichlorostilbene (4dd). oil; $^1$H NMR: δ 7.13 (m, 2H), 7.35 (m, 6H), 7.54 (d, 2H, J=7.54 Hz). Exact mass calcd for C$_{14}$H$_{10}$Cl$_2$:298.1569, observed (M+H) 299.1647.

(E)-2,4',6-Trimethoxystilbene (6g). mp 45-46° C.; $^1$H NMR: δ 3.72 (s, 3H), 3.79 (s, 6H), 6.49 (d, 2H, J=8.34 Hz), 6.79 (d, 2H, J=8.74 Hz), 7.05 (t, 1H, J=8.34 Hz), 7.24 (d, 1H, J=16.68 Hz) 7.39 (d, 2H, J=8.74 Hz), 7.45 (d, 1H, J=16.48 Hz). Exact mass calcd for C$_{17}$H$_{18}$O$_3$:270.1256 observed (M+H) 271.1334.

(E)-2,3,4,4'-Tetramethoxystilbene (6s). mp 124-125° C.; $^1$H NMR: δ 3.81 (s, 3H), 3.86 (s, 3H), 3.89 (s, 6H), 6.68 (d, 1H, J=8.74 Hz), 6.88 (d, 2H, J=8.74 Hz), 6.96 (d, 1H, J=16.68 Hz), 7.19 (d, 1H, J=16.29 Hz), 7.27 (d, 1H, J=8.74 Hz), 7.44 (d, 2H, J=8.74 Hz). Exact mass calcd for C$_{18}$H$_{20}$O$_4$: 300.1362, observed (M+H) 301.1440.

(E)-2-Ethyl-3,4,4'-trimethoxystilbene (6v). mp 97-98° C.; $^1$H NMR: δ 1.17 (t, 3H, J=7.55 Hz), 2.80 (q, 2H, J=7.54 Hz), 3.81 (s, 3H), 3.82 (s, 3H), 3.86 (s, 3H), 6.78 (m, 2H) 6.87 (m, 3H), 7.14 (d, 1H, J=15.89 Hz), 7.31 (d, 1H, J=8.54 Hz), 7.42 (d, 2H, J=8.54 Hz); $^{13}$C NMR: δ 15.4, 19.7, 55.4, 55.8, 60.9, 110.1, 114.1, 121.2, 124.1, 127.5, 128.4, 129.9, 130.8, 136.2, 146.8, 152.0, 159.0. Exact mass calcd for C$_{19}$H$_{22}$O$_3$:298.1569, observed (M+H) 299.1647.

(E)-3-Bromo-4'-methoxystilbene (6w). mp 114-115° C.; $^1$H NMR: δ 3.18 (s, 3H), 6.87 (m, 3H), 7.04 (d, 1H, J=16.28 Hz), 7.18 (t, 1H, J=7.75 Hz), 7.35 (m, 2H), 7.43 (d, 2H, J=8.74 Hz), 7.63 (s, 1H). Exact mass calcd for C$_{15}$H$_{13}$BrO: 288.0150, observed (M+H) 289.0228.

(E)-2-Trifluoromethyl-4'-methoxystilbene (6z). oil; $^1$H NMR: δ 3.80 (s, 3H), 6.89 (d, 2H, J=8.74 Hz), 7.01 (d, 1H, J=16.10 Hz), 7.31 (m, 2H), 7.48 (m, 3H) 7.63 (d, 1H, J=7.74 Hz), 7.74 (d, 1H, J=7.75 Hz). Exact mass calcd for C$_{16}$H$_{13}$F$_3$O:278.0918, observed (M+H) 279.0996.

(E)-4'-Methoxy-2,4,6-trimethylstilbene (6aa). mp 68-69° C.; $^1$H NMR: δ 2.28 (s, 3H), 2.33 (s, 6H), 3.82 (s, 3H), 6.51 (d, 1H, J=16.69 Hz), 6.91 (m, 5H), 7.42 (d, 2H, J=8.73 Hz). Exact mass calcd for C$_{18}$H$_{20}$O:252.1514, observed (M+H) 253.1592.

(E)-2,3-Dihydroxy-4'-methoxystilbene (6cc). mp 125-126° C.; $^1$H NMR: δ 3.82 (s, 3H), 5.18 (s, 1H), 5.54 (s, 1H), 6.75 (m, 2H), 6.88 (d, 2H, J=8.74 Hz), 7.07 (m, 2H), 7.19 (d, 1H, J=16.29 Hz), 7.45 (d, 2H, J=8.73 Hz). Exact mass calcd for C$_{15}$H$_{14}$O$_3$:242.0943, observed (M+H) 243.1021.

General methods for synthesis of benzyl phosphonic acid diethyl esters and MOM-protected hydroxybenzaldehydes, physical and spectroscopic data for reported compounds 4a-4f, 4h-4r, 4t-4y, 4aa-4cc, 4ee-4gg, 6a-6f, 6h-6r, 6t, 6u, 6x, 6y, 6bb, 6dd, 6ee, 8a-8j appears below.

Unless otherwise noted all reagents were obtained from commercial sources and used without further purification. All compounds that were isolated were greater than 90% pure by $^1$H and/or $^{13}$C NMR. Column chromatographic separations were performed using EM Science type 60 silica gel (230-400 mesh). Melting points were determined on a Thomas Hoover capillary melting point apparatus and are uncorrected. NMR spectra were recorded on a Bruker AC250 (250 MHz) NMR spectrometer in CDCl$_3$ unless otherwise noted. Chemical shifts are reported in ppm (δ) relative to CHCl$_3$ at 7.24 ppm for $^1$H NMR and 77.0 for $^{13}$C NMR. High resolution mass spectra were performed at the Mass Spectrometry Facility, University of New Mexico.

General method for the preparation of substituted benzyl phosphonic acid diethyl esters. Substituted benzyl bromide was heated with excess triethylphosphite at 140° C. until the evolution of bromoethane had ceased and complete dissolution occurred. The remaining triethylphosphite was then removed by concentration of the solution in vacuo to afford the product.

General method for the preparation of MOM protected aidehydes.

To a suspension of hexane rinsed sodium hydride (1.5 equivalents) in dimethyl formamide is added a solution of the appropriate aldehyde (1 equivalent) in dimethyl formamide. After stirring 2 hours at room temperature dichloromethylmethyl ether is added and the solution is stirred an additional 3 hours at room temperature. The solution is quenched by pouring over ice water and extracted with ether. The ether extracts are washed with 1M sodium hydroxide, saturated sodium chloride and dried with magnesium sulfate, filtered and evaporated to give a crude oil that is distilled bulb to bulb to afford the product as a solid.

(E)-3,4-Dimethoxystilbene (4a). mp 108-109° C. [lit.[1] 112-113° C.].

(E)-4-Methoxystilbene (4b). mp 134-135° C. [lit.[2] 135-136° C.].

(E)-4-Chlorostilbene (4c). mp 129-130° C. [lit.[3] 129-131° C.].

(E)-4-Methylstilbene (4d). mp 114-116° C. [lit.[3] 118-120° C.].

(E)-4-Cyanostilbene (4e). mp 116-117° C. [lit.[3] 115-118° C.].

(E)-3,5-Dimethoxystilbene (4f). mp 53-55° C. [lit.[4] 54-55° C.].

(E)-3-Chlorostilbene (4h). mp 74-76° C. [lit.[5] 71-72.5° C.].

(E)-3-Methylstilbene (4i). mp 50-51° C. [lit.[6] 48-49° C.].

(E)-2-Chlorostilbene (4j). mp 64-66° C. [lit.[7] 37-38° C.].

(E)-4-Ethoxystilbene (4k). mp 124-126° C. [lit.[8] 77-78° C.].

(E)-4-Hydroxystilbene (4l). mp 183-185° C. [lit.[9] 188° C.].

(E)-4-Fluorostilbene (4m). mp 123-124° C. [lit.[10] 124° C.].

(E)-3-Fluorostilbene (4n). mp 74-76° C. [lit.[11] 70-72° C.].

(E)-2,3-Dimethoxystilbene (4o). mp 37-39° C. [lit.[12] 38-39° C.].

(E)-2-Fluorostilbene (4p). mp 103-105° C. [lit.[13] 102-103° C.].

(E)-4-Hydroxy-3-methoxystilbene (4q). mp 133-134° C. [lit.[9] 138° C.].

(E)-3-Methoxystilbene (4r). mp 34-35° C. [lit.[2] 34-35° C.].

(E)-3-Hydroxystilbene (4t). mp 119-121° C. [lit.[14] 119-120° C.].

(E)-2,4-Dimethoxystilbene (4u). mp 64-65° C. [lit.[15] 64.5-65° C.].

(E)-2-Methylstilbene (4v). mp 35-36° C. [lit.[2] 28-29° C.].

(E)-3-Trifluoromethylstilbene (4w). mp 67-68° C. [lit.[16] 66-67° C.].

(E)-4-Trifluoromethylstilbene (4x). mp 133-134° C. [lit.[2] 134-135° C.].

(E)-2,5-Dimethoxystilbene (4y). oil; $^1$H NMR: δ 3.81 (s, 3H), 3.83 (s, 3H), 6.80 (m, 2H), 7.09 (d, 1H, J=16.48 Hz), 7.16 (d, 1H, J=2.38 Hz), 7.25 (m, 1H), 7.34 (t, 2H, J=7.35 Hz), 7.47 (d, 1H, J=16.49 Hz), 7.53 (d, 2H, J=7.15 Hz).

(E)-2,4,6-Trimethylstilbene (4aa). mp 56-57° C. [lit.[17] 49-50° C.].

(E)-2-Methoxystilbene (4bb). mp 58-59° C. [lit.[2] 56-57° C.].

(E)-4-N,N-Dimethylaminostilbene (4cc). mp 144-146° C. [lit.[18] 150° C.].

(E)-3,4-Dihydroxystilbene (4ee). mp 167-168° C. [lit.[19] 168-169° C.].

(E)-3,4,5-Trimethoxystilbene (4ff). mp 107-108° C. [lit.[20] 105-106° C.].

(E)-2,3,4-Trimethoxystilbene (4gg). mp 80-83° C. [lit.[20] 79-82° C.].

(E)-3,4,4'-Trimethoxystilbene (6a). mp 136-138° C. [lit.[4] 136-138° C.].

(E)-4,4'-Dimethoxystilbene (6b). mp 212-213° C. [lit.[2] 214-216° C.].

(E)-4-Chloro-4'-methoxystilbene (6c). mp 181-183° C. [lit.[4] 181-184° C.].

(E)-4'-Methoxy-4-methylstilbene (6d). mp 160-162° C. [lit.[21] 166-167° C.].

(E)-4-Cyano-4'-methoxystilbene (6e). mp 141-143° C. [lit.[22] 141-142 ° C.].

(E)-3,4',5-Trimethoxystilbene (6f). mp 53-55° C. [lit.[4] 53-56° C.].

(E)-3-Chloro-4'-methoxystilbene (6h). mp 93-94° C. [lit.[21] 96° C.].

(E)-4'-Methoxy-3-methylstilbene (6i). mp 110-111° C. [lit.[21] 98° C.].

(E)-2-Chloro-4'-methoxystilbene (6j). mp 52-53° C. [lit.[23] 59-60° C.].

(E)-4-Ethoxy-4'-methoxystilbene (6k). mp 194-195° C. [lit.[24] 165-167° C.].

(E)-3,4,4',5-Tetramethoxystilbene (6l). mp 157-159° C. [lit.[20] 152-155° C.].

(E)-4-Fluoro-4'-methoxystilbene (6m). mp 148-150° C. [lit.[25] 147-149° C.].

(E)-3-Fluoro-4'-methoxystilbene (6n). mp 108-110° C. [lit.[11] 108-110° C.].

(E)-2,3,4'-Trimethoxystilbene (6o). mp 70-72° C. [lit.[26] 73-74° C.].

(E)-2-Fluoro-4'-methoxystilbene (6p). mp 100-101° C. [lit.[13] 102-103° C.].

(E)-2,4,4',5-Tetramethoxystilbene (6q). mp 106-107° C. [lit.[27] 110° C.].

(E)-3,4'-Dimethoxystilbene (6r). mp 107-108° C. [lit.[26] 107-108° C.].

(E)-4-Bromo-4'-methoxystilbene (6t). mp 200-201° C. [lit.[28] 177-179° C.].

(E)-2,4,4'-Trimethoxystilbene (6u). mp 94-95° C. [lit.[29] 89° C.].

(E)-3,4-Dihydroxy-4'-methoxystilbene (6x). mp d 186° C. [lit.[30]]; $^1$H NMR: (DMSO-d$_6$) δ 3.75 (s, 3H), 6.70 (d, 1H, J=8.94 Hz), 6.87 (m, 6H), 7.45 (d, 2H, J=8.34 Hz), 8.88 (s, 1H), 9.00 (s, 1H).

(E)-2,4',5-Trimethoxystilbene (6y). mp 67-68° C. [lit.[31] oil]; $^1$H NMR: δ 3.80 (s, 3H), 3.81 (s, 3H), 3.82 (s, 3H), 6.80 (m, 2H), 6.88 (d, 2H, J=8.74 Hz), 7.04 (d, 1H, J=16.48 Hz), 7.13 (d, 1H, J=2.78 Hz), 7.32 (d, 1H, J=16.48 Hz), 7.47 (d, 2H, J=8.74 Hz).

(E)-2,4'-Dimethoxystilbene (6bb). mp 89-90° C. [lit.[32] 85-86° C.].

(E)-4'-Methoxy-4-N,N-dimethylaminostilbene (6dd). mp 182-183° C. [lit.³³ 185-186° C.].
(E)-2,6-Dichloro-4'-methoxystilbene (6ee). mp 56-60° C.; ¹H NMR: δ 3.83 (s, 3H), 6.92 (d, 2H, J=8.74 Hz), 7.05 (m, 3H), 7.33 (d, 2H, J=7.94 Hz), 7.49 (d, 2H, J=8.54 Hz).
(E)-3-Stilbazole (8a). mp 81-82° C. [lit.³⁴ 83-85° C.].
(E)-4-Stilbazole (8b). mp 124-126° C. [lit.³⁵ 128° C.].
(E)-2-Stilbazole (8c). mp 89-91° C. [lit.³⁶ 93° C.].
(E)-2-Styrylthiophene (8d). mp 111-112° C. [lit.³⁶ 112-113° C.].
(E)-2-Styrylnaphthalene (8e). mp 147-148° C. [lit.³⁷ 147-148° C.].
(E)-1-Styrylnaphthalene (8f). mp 71-72° C. [lit.³⁸ 71-72° C.].
(E)-2-(4-Methoxystyryl)naphthalene (8g). mp 172-173° C. [lit.³⁹ 142° C.].
(E)-1-(4-Methoxystyryl)naphthalene (8h). mp 93-94° C. [lit.⁴⁰ 92-93° C.].
(E)-2-(4-Methoxystyryl)thiophene (8i). mp 133-134° C. [lit.⁴¹ 134-135° C.].
(E)-4'-Methoxy-3-stilbazole (8j). mp 98-100° C. [lit.⁴² 99-100° C.].

Compound 3 (Z-stilbene) of Scheme 4

To 1 mmol of the phosphonium salt (1) dissolved in 2 mL of dichloromethane, the aryl aldehyde (2, 1 mmol) and 18-crown-6 (0.05-0.1 mmol) were added. The mixture was cooled to −70° C. and freshly powdered potassium hydroxide (2 mmol) was added under stirring. The reaction was stirred at −40° C. until tlc indicated complete reaction. The mixture was diluted with dichloromethane and water. The dichloromethane layer was separated washed with water, saturated salt solution and dried over magnesium sulfate. Filtration and evaporation afforded a crude product (3) that was purified by preparative thin layer chromatography. A number of analogs are synthesized using this general method and tested in the NF-κB assay. See FIG. 13. Also, see, Bellucci, G.; Chiappe, C.; Lo Moro, G. *Tetrahedron Lett.*, 1996, 37, 4225-4228.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

REFERENCES

1. Yamamoto, Y.; Gaynor, R. B. Therapeutic potential of inhibition of the NF-kappaB pathway in the treatment of inflammation and cancer. *J. Clin. Invest.* 2001, 107, 135-142.
2. Kim, H. J.; Hawke, N.; Baldwin, A. S. NF-κB and IKK as therapeutic targets in cancer. *Cell Death Different.* 2006, advanced online publication.
3. Kaltschmidt, B.; Widera, D.; Kaltschmidt, C. Signaling via NF-κB in the nervous system. *Biochim. Biophys. Acta* 2005, 1745, 287-299.
4. Viatour, P.; Merville, M-P.; Bours, V.; Chariot, A. Phosphorylation of NF-kappaB and IkappaB proteins: implications in cancer and inflammation. *Trends Biochem. Sci.* 2005, 30, 43-52.
5. Kumar, A.; Takada, Y.; Boriek, A. M.; Aggarwal, B. B. Nuclear factor-κb: its role in health and disease. *J. Mol. Med.* 2004, 82, 434-448.
6. Hiscott, J.; Kwon, H.; Genin, P. Hostile takeovers: viral appropriation of the NF-kappaB pathway. *J. Clin. Invest.* 2001, 107, 143-151.
7. Barkett, M.; Gilmore, T. Control of apoptosis by Rel/NF-kappaB transcription factors. *Oncogene* 1999, 18, 6910-6924.
8. Karin, M.; Greten, F. R. NF-κB: linking inflammation and immunity to cancer development and progression. *Nature Rev. Immunol* 2005, 5, 749-759.
9. Herrmann, O.; Baumann, B.; de Lorenzi, R.; Muhammad, S.; Zhang, W.; Kleesiek, J.; Malfertheiner, M.; Kohrmann, M.; Potrovita, I.; Maegele, I.; Beyer, C.; Burke, J. R.; Hasan, M. T.; Bujard, H.; Wirth, T.; Pasparakis, M.; Schwaninger, M. IKK mediates ischemia-induced neuronal death. *Nat. Med.* 2005, 11, 1322-1329.
10. Schmitz, M. L.; Mattioli, I.; Buss, H.; Kracht, M. NF-κB: a multifaceted transcription factor regulated at several levels. *ChemBioChem* 2004, 5, 1348-1358.
11. http://people.bu.edu/gilmore/nf-kb/inhibitors
12. Dore, S. Unique properties of polyphenol stilbenes in the brain: more than direct antioxidant actions; gene/protein regulatory activity. *Neurosignals* 2005, 14, 61-70.
13. Kundu, J. K.; Surh, Y-J. Molecular basis of chemoprevention by resveratrol: NF-κB and AP-1 as potential targets. *Mut. Res.* 2004, 555, 65-80.
14. Shimizu, M.; Weinstein, B. Modulation of signal transduction by tea catechins and related phytochemicals. *Mut. Res.* 2005, 591, 147-160.
15. Renaud, S.; de Lorgeril, M. Wine, platelets, and the French paradox for coronary heart disease. *Lancet* 1992, 339, 1523-1526.
16. Jang, M.; Cai, L.; Udeani, G. O.; Slowing, K. V.; Thomas, C. F.; Beecher, C. W.; Fong, H. H.; Farnsworth, N. R.; Kinghorn, A. D.; Mehta, R. G.; Moon, R. C.; Pezzuto, J. M. Cancer chemopreventive activity of resveratrol, a natural product derived from grapes. *Science* 1997, 275, 218-220.
17. Ovesna, Z.; Horvathova-Kozics, K. Structure-activity relationship of trans-resveratrol and its analogs. *Neoplasma* 2005, 52, 450-455.
18. Orallo, F. Comparative studies of the antioxidant effects of cis- and trans-resveratrol. *Curr. Med. Chem.* 2006, 13, 87-98.
19. Lu, M.; Cai, Y. J.; Fang, J. G.; Zhou, Y. L.; Liu, Z. L.; Wu, L. M. Efficiency and structure-activity relationship of the antioxidant action of resveratrol and its analogs. *Pharmazie* 2002, 57, 474-478.
20. Stojanovic, S.; Sprinz, H.; Brede, O. Efficiency and mechanism of the antioxidant action of trans-resveratrol and its analogues in the radical liposome oxidation. *Arch. Biochem. Biophys.* 2001, 391, 79-89.
21. Stivala, L. A.; Savio, M.; Carafoli, F.; Perucca, P.; Bianchi, L.; Maga, G.; Forti, L.; Pagnoni, U. M.; Albini, A.; Prosperi, E.; Vannini, V. Specific structural determinants are responsible for the antioxidant activity and the cell cycle effects of resveratrol. *J. Biol. Chem.* 2001, 276, 22586-22594.
22. Chung, M. I.; Teng, C. M.; Cheng, K. L.; Ko, F. N.; Lin, C. N. An antiplatelet principle of Veratrum formosanum. *Planta Med.* 1992, 58, 274-276.

23. Fremont, L.; Gozzelino, M. T.; Linard, A. Response of plasma lipids to dietary cholesterol and wine polyphenols in rats fed polyunsaturated fat diets. *Lipids* 2000, 35, 991-999.
24. Murias, M.; Handler, N.; Erker, T.; Pleban, K.; Ecker, G.; Saiko, P.; Szekeres, T.; Jager, W. Resveratrol analogues as selective cyclooxygenase-2 inhibitors: synthesis and structure-activity relationship. *Bioorg. Med. Chem.* 2004, 12, 5571-5578.
25. Shay, N. F.; Banz, W. J. Regulation of gene transcription by botanicals: novel regulatory mechanisms. *Annu. Rev. Nutr.* 2005, 25, 297-315.
26. Juan, S. H.; Cheng, T. H.; Lin, H. C.; Chu, Y. L.; Lee, W. S. Mechanism of concentration-dependent induction of heme oxygenase-1 by resveratrol in human aortic smooth muscle cells. *Biochem. Pharmacol.* 2005, 69, 41-48.
27. Kundu, J. K.; Shin, Y. K.; Surh, Y. J. Resveratrol inhibits phorbol ester-induced expression of COX-2 and activation of NF-kappaB in mouse skin by blocking IkappaB activity. *Carcinogenesis* 2006, Epub ahead of print.
28. Lee, B.; Moon, S-K. Resveratrol inhibits TNF-κ-induced proliferation and matrix metalloproteinase expression in human vascular smooth muscle cells. *J. Nutr.* 2005, 135, 2767-2773.
29. Liao, H. F.; Kuo, C. D.; Yang, Y. C.; Lin, C. P.; Tai, H. C.; Chen, Y. Y.; Chen, Y. J. Resveratrol enhances radiosensitivity of human non-small cell lung cancer NCI-H838 cells accompanied by inhibition of nuclear factor-kappa B activation. *J. Radiat. Res. (Tokyo)* 2005, 46, 387-393.
30. Bi, X. L.; Yang, J. Y.; Dong, Y. X.; Wang, J. M.; Cui, Y. H.; Ikeshima, T.; Zhao, Y. Q.; Wu, C. F. Resveratrol inhibits nitric oxide and TNF-alpha production by lipopolysaccharide-activated microglia. *Int. Immunopharmacol.* 2005, 5, 185-193.
31. Bellucci, G.; Chiappe, C.; Lo Moro, G. Crown ether catalyzed stereospecific synthesis of Z- and E-stilbenes by Wittig reaction in a solid-liquid two-phase system. *Tetrahedron Lett.* 1996, 37, 4225-4228.
32. Lion, C. J.; Matthews, C. S.; Stevens, M. F. G.; Westwell, A. D. Synthesis, antitumor evaluation, and apoptosis-inducing activity of hydroxylated (E)-stilbenes. *J. Med. Chem.* 2005, 48, 1292-1295.
33. Kang, G.; Kong, P. J.; Yuh, Y. J.; Lim, S. Y.; Yim, S. V.; Chun, W.; Kim, S. S. Curcumin suppresses lipopolysaccharide-induced cyclooxygenase-2 expression by inhibiting activator protein 1 and nuclear factor kappab bindings in BV2 microglial cells. *J. Parmaco.l Sci.* 2004, 94, 325-328.
34. Wieder, T.; Prokop, A.; Bagci, B.; Essmann, F.; Bernicke, D.; Schulze-Osthoff, K.; Dorken, B.; Schmalz, H. G.; Daniel, P. T.; Henze, G. Piceatannol, a hydroxylated analog of the chemopreventive agent resveratrol, is a potent inducer of apoptosis in the lymphoma cell line BJAB and in primary, leukemic lymphoblasts. *Leukemia* 2001, 15, 1735-1742.
35. Ashikawa, K.; Majumdar, S.; Banerjee, S.; Bharti, A. C.; Shishodia, S.; Aggarwal, B. B. Piceatannol inhibits TNF-induced NF-κB activation and NF-κB-mediated gene expression through suppression of IκBκ kinase and p65 phosphorylation. *J. Immunol.* 2002, 169, 6490-6497.
36. Rimando, A. M.; Cuendet, M.; Desmarchelier, C.; Mehta, R. G.; Pezzuto, J. M.; Duke, S. O. Cancer chemopreventive and antioxidant activities of pterostilbene, a naturally occurring analogue of resveratrol. *J. Agric. Food Chem.* 2002, 50, 3453-3457.
37. Tolomeo, M.; Grimaudo, S.; Di Cristina, A.; Roberti, M.; Pizzirani, D.; Meli, M.; Dusonchet, L.; Gebbia, N.; Abbadessa, V.; Crosta, L.; Barucchello, R.; Grisolia, G.; Invidiata, F.; Simoni, D. Pterostilbene and 3'-hydroxypterostilbene are effective apoptosis-inducing agents in MDR and BCR-ABL-expressing leukemia cells. *Int. J. Biochem. Cell. Biol.* 2005, 37, 1709-1726.
38. Mann, S. K.; Mukhopadhyay, A.; Aggarwal, B. B. Resveratrol suppresses TNF-induced activation of nuclear transcription factors NF-κB, activator protein-1, and apoptosis: potential role of reactive oxygen intermediates and lipid peroxidation. *J. Immunol.* 2000, 164, 6509-6519.
39. Sizemore, N.; Lerner, N.; Dombrowski, N.; Sakurai, H.; Stark, G. R. Distinct roles of the IκB kinase a and b in liberating nuclear factor κB (NF-κB) from IB and in phosphorylating the p65 subunit of NF-κB. *J. Biol. Chem.* 2002, 277, 3863-3869.
40. Schlesier, K.; Harwat, M.; Bohm, V.; Bitsch, R. Assessment of antioxidant activity by using different in vitro methods. *Free Rad. Res.* 2002, 36, 177-187.
41. Re, R.; Pellegrini, N.; Proteggente, A.; Pannala, A.; Yang, M.; Rice-Evans, C. Antioxidant activity applying an improved ABTS radical cation decolorization assay. *Free Rad. Biol. Med.* 1999, 26, 1231-1237.
42. Benzie, I. F.; Strain, J. J. Ferric reducing/antioxidant power assay: direct measure of total antioxidant activity of biological fluids and modified version for simultaneous measurement of total antioxidant power and ascorbic acid concentrations. *Methods Enzymol.* 1999, 299, 15-27.
43. Begum, S. D.; Parthasarathi, J. A convenient synthesis of homobutein. *Ind. J. Chem., Sect. B* 1988, 27B, 464.

What is claimed is:

1. A method of treating Alzheimer's disease in a patient in need, the method comprising administering to the patient a composition comprising a therapeutically effective amount of at least one compound selected from the group consisting of (E)-4-Ethoxystilbene (4k), (E)-4-N,N-Dimethylaminostilbene (4cc), (E)-3,4'-Dimethoxystilbene (6r), (E)-4'-Methoxy-3-methylstilbene (6i), (E)-2-Fluoro-4'-methoxystilbene (6p), (E)-3-Fluoro-4'-methoxystilbene (6n), (E)-4-Fluoro-4'-methoxystilbene (6m), (E)-3-Chloro-4'-methoxystilbene (6h) and (E)-4'-Methoxy-4-methylstilbene (6d), or a pharmaceutically acceptable salt, hydrate or solvate thereof, optionally in combination with a pharmaceutically acceptable carrier, additive or excipient.

2. The method according to claim 1 wherein said compound inhibits NF-κB activity.

3. The method according to claim 1 wherein the compound inhibits AP-1 activity.

4. The method according to claim 1 wherein the compound inhibits NF-κB activity and AP-1 activity.

5. The method according to claim 1 wherein said at least one compound is selected from the group consisting of (E)-4-Ethoxystilbene (4k), (E)-4-N,N-Dimethylaminostilbene (4cc), (E)-3,4'-Dimethoxystilbene (6r), (E)-4'-Methoxy-3-methylstilbene (6i), (E)-2-Fluoro-4'-methoxystilbene (6p), and (E)-4-Fluoro-4'-methoxystilbene (6m), or a pharmaceutically acceptable salt, hydrate or solvate thereof.

6. The method according to claim 1 wherein said at least one compound is selected from the group consisting of (E)-4-Ethoxystilbene (4k), (E)-4-N,N-Dimethylaminostilbene (4cc), (E)-3,4'-Dimethoxystilbene (6r), (E)-3-Fluoro-4'-methoxystilbene (6n) and (E)-2-Fluoro-4'-methoxystilbene (6p), or a pharmaceutically acceptable salt, hydrate or solvate thereof.

7. The method according to claim 1 wherein said at least one compound is selected from the group consisting of (E)-4-Ethoxystilbene (4k), (E)-4-N,N-Dimethylaminostilbene (4cc), (E)-3,4'-Dimethoxystilbene (6r) and (E)-2-Fluoro-4'-methoxystilbene (6p), or a pharmaceutically acceptable salt, hydrate or solvate thereof.

8. The method according to claim 1 wherein said at least one compound is selected form the group consisting of (E)-4-Ethoxystilbene (4k) and (E)-2-Fluoro-4'-methoxystilbene (6p), or a pharmaceutically acceptable salt, hydrate or solvate thereof.

9. The method according to claim 1 wherein said at least one compound is selected from the group consisting of (E)-4-N,N-Dimethylaminostilbene (4cc), (E)-3,4'-Dimethoxystilbene (6r), and (E)-2-Fluoro-4'-methoxystilbene (6p), or a pharmaceutically acceptable salt, hydrate or solvate thereof.

10. The method according to claim 1 wherein said at least one compound is selected from the group consisting of (E)-4-Ethoxystilbene (4k), (E)-4-N,N-Dimethylaminostilbene (4cc), (E)-3-Fluoro-4'-methoxystilbene (6n) and (E)-2-Fluoro-4'-methoxystilbene (6p), or a pharmaceutically acceptable salt, hydrate or solvate thereof.

11. The method according to claim 1 wherein said at least one compound is (E)-2-Fluoro-4'-methoxystilbene (6p) or a pharmaceutically acceptable salt, hydrate or solvate thereof.

12. The method according to claim 1 wherein said compound is administered by oral delivery.

13. The method according to claim 1 wherein said compound is administered by topical delivery.

14. A method of treating Alzheimer's disease in a patient in need, the method comprising administering to the patient a composition comprising a therapeutically effective amount of (E)-2-Fluoro-4'-methoxystilbene (6p), or a pharmaceutically acceptable salt thereof, optionally in combination with a pharmaceutically acceptable carrier, additive or excipient.

15. The method according to claim 14 wherein said compound is administered by oral delivery.

16. The method according to claim 14 wherein said compound is administered by topical delivery.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: synthetic sequence

<400> SEQUENCE: 1
tggggtgatg agcaactatt                                              20

<210> SEQ ID NO 2
<211> LENGTH: 20
<212> TYPE: DNA
```

```
<213> ORGANISM: Artificial Sequence
<220> FEATURE:
<223> OTHER INFORMATION: synthetic sequence

<400> SEQUENCE: 2
aaggagctct gggtcaaact                                              20
```